(12) United States Patent
Rolfs et al.

(10) Patent No.: US 10,690,682 B2
(45) Date of Patent: Jun. 23, 2020

(54) METHOD FOR THE DIAGNOSIS OF METACHROMATIC LEUKODYSTROPHY

(71) Applicant: CENTOGENE AG, Rostock (DE)

(72) Inventors: Arndt Rolfs, Berlin (DE); Hermann Mascher, Traiskirchen (AT)

(73) Assignee: Centogene AG, Rostock (DE)

( * ) Notice: Subject to any disclaimer, the term of this patent is extended or adjusted under 35 U.S.C. 154(b) by 0 days.

(21) Appl. No.: 14/651,450

(22) PCT Filed: Dec. 11, 2013

(86) PCT No.: PCT/EP2013/003750
§ 371 (c)(1),
(2) Date: Jun. 11, 2015

(87) PCT Pub. No.: WO2014/090404
PCT Pub. Date: Jun. 19, 2014

(65) Prior Publication Data
US 2015/0316563 A1    Nov. 5, 2015

(30) Foreign Application Priority Data

Dec. 11, 2012 (EP) .................................... 12008257
Dec. 12, 2012 (EP) .................................... 12008293
Mar. 21, 2013 (EP) .................................... 13001454

(51) Int. Cl.
*G01N 33/68*    (2006.01)
(52) U.S. Cl.
CPC ..... *G01N 33/6893* (2013.01); *G01N 2800/04* (2013.01)
(58) Field of Classification Search
CPC ............... G01N 33/92; G01N 2800/52; G01N 33/6893; G01N 2405/10; G01N 2560/00; G01N 2800/50; G01N 2800/04
See application file for complete search history.

(56) References Cited

FOREIGN PATENT DOCUMENTS

EP    2 743 700 A1    6/2014

OTHER PUBLICATIONS

Toda et al. Lysosulfatide (Sulfogalactosylsphingosine) accumulation in tissues from patients with metachromatic leukodystrophy. J. Neurochemistry 1990, vol. 55, No. 5, pp. 1585-1591.*
William W. Christie, Glycosphingolipid sulfates. Structure, occurrence, biology and analysis. James Hutton Institute, Invergowire, Dundee, Scotland, 2012, pp. 1-4.*
Blomqvist et al. Accumulation of lysosulfatide in the brain of arylsulfatase A—deficient mice. Lipids in Health and Disease 2011, vol. 10, No. 28, pp. 1-5.*
McCann et al. Measurement of total homocysteine in plasma and blood spots using liquid chromatography-tandem mass spectrometry: comparison with the plasma Abott IMx method. Ann CLin. Biochem. 2003, vol. 40, pp. 161-165.*
Mirzaian, Mina. The development of an UPLC-MS/MS method for determination of lysoglobotriaosylceramide (lysoGb3) and (lyso)-sulfatide in body fluids and tissues from patients with Fabry disease and metachromatic leukodystropy (MLD). Master's Thesis 2011, University of Amsterdam, Faculty of Science, Dept. of Medical Biochemistry. pp. 1-61.*
Mcdade et al. What a drop can do: dried blood spots as a minimally invasive method for integrating biomarkers into population-based research. Demography, 2007, vol. 44, No. 4, pp. 899-925.*
International Search Report dated Apr. 11, 2014 from PCT International Application No. PCT/EP2013/003750.
Christopher, R., et al., "Serum arylsulfatase A assay in metachromatic leukodystrophy: An experience in a neuropsychiatric set-up," Indian Journal of Clinical Biochemistry 1995 IN, vol. 10, No. 2, 1995, pp. 89-92.
Griffiths, P. A., et al., "Plasma acid hydrolases in normal adults and children, and i patients with some lysosomal storage diseases," Clinical Chimica Acta, Elsevier BV, Amsterdam, NL, vol. 90, No. 2, Dec. 1, 1978, pp. 129-141.
Mirzaian, M., "The development of an UPLC-MS/MS method for determination of lysoglobotriaosylceramide (lysoGb3) and (lyso)-sulfatide in body fluids and tissues from patients with Fabry disease and metachromatic leukodystrophy (MLD)," Master Chemistry Thesis, University of Amsterdam, Mar. 1, 2011, pp. 21-54.
Toda, K., et al., "Accumulation of lysosulfatide (sulfagalactosylsphingosine) in tissues of a boy with metachromatic leukodystrophy," Biochemical and Biophysical Research Communications, Academic Press, Inc., Orlando, FL, US, vol. 159, No. 2, Mar. 15, 1989, pp. 605-611.
Rosengren, B., et al., "Lysosulfatide (galactosylsphingosine-3-0-sulfate) from metachromatic leukodystrophy and normal human brain," Journal of Neurochemistry Apr. 1989, vol. 52, No. 4, Apr. 1989, pp. 1035-1041.
Communication pursuant to Article 94(3) EPC, European Patent Application No. 13 815 378.8, dated Feb. 8, 2017, 6 pages.

* cited by examiner

*Primary Examiner* — Shafiqul Haq
(74) *Attorney, Agent, or Firm* — Stanek Lemon Crouse & Meeks, PA

(57) ABSTRACT

The present invention is related to a method for diagnosing metachromatic leukodystrophy in a subject comprising a step a), wherein the step a) comprises detecting a biomarker in a sample from the subject, wherein the sample is selected from the group consisting of blood, dried blood, serum and plasma and wherein the biomarker is different from an enzyme.

3 Claims, 8 Drawing Sheets

Fig. 1A (1)
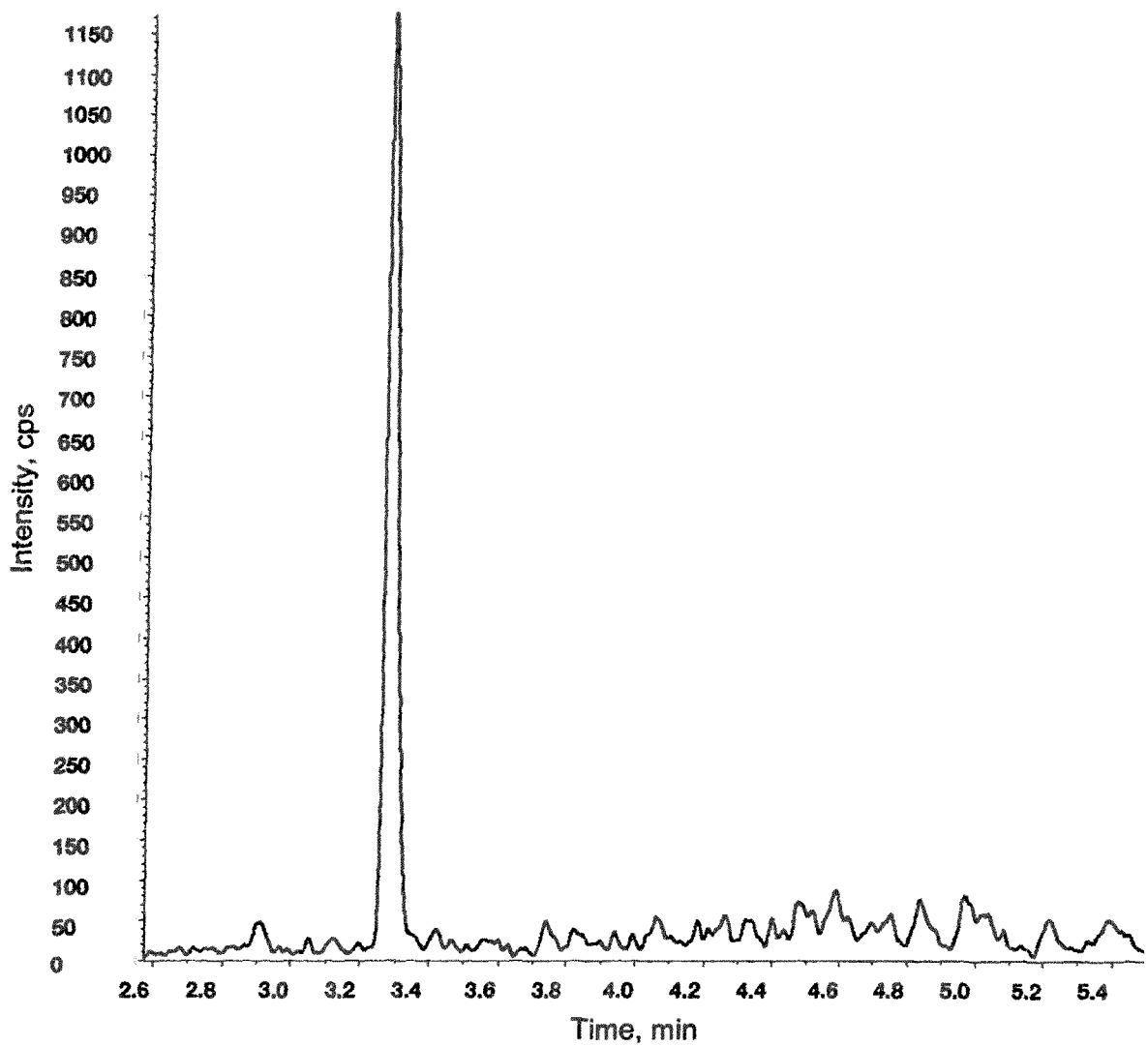

Fig. 1A (2)
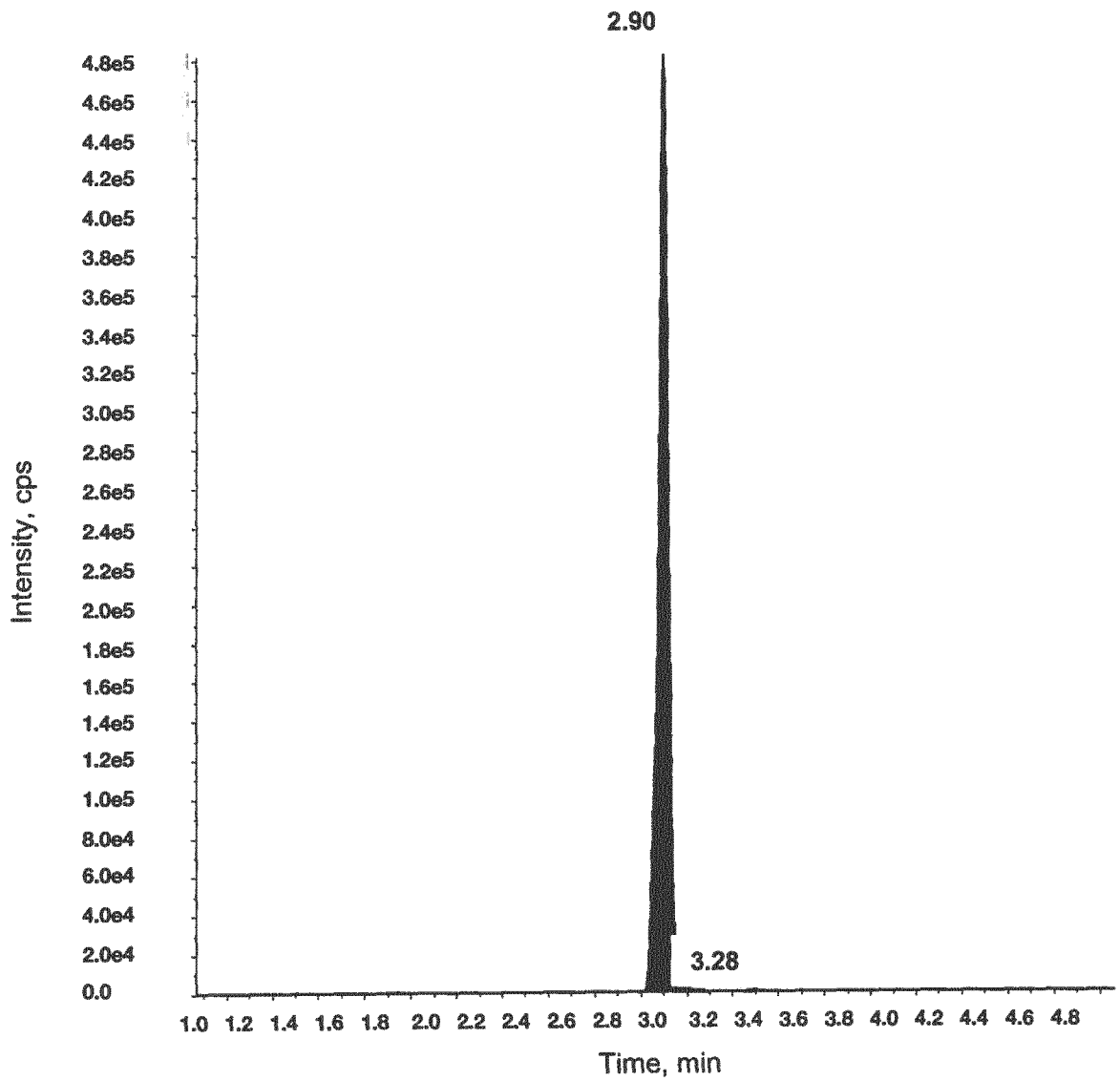

Fig. 1B (1)
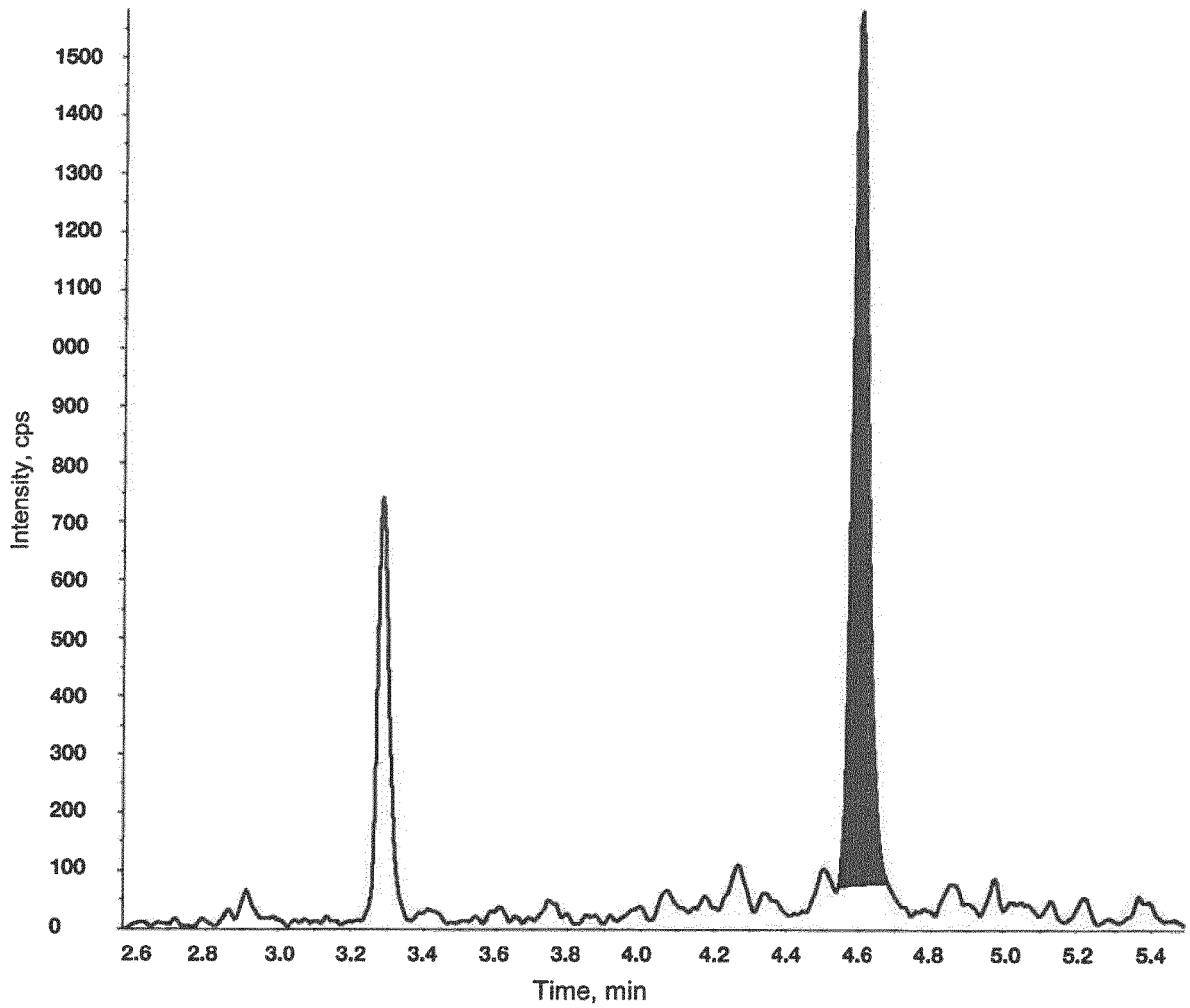

Fig. 1B (2)
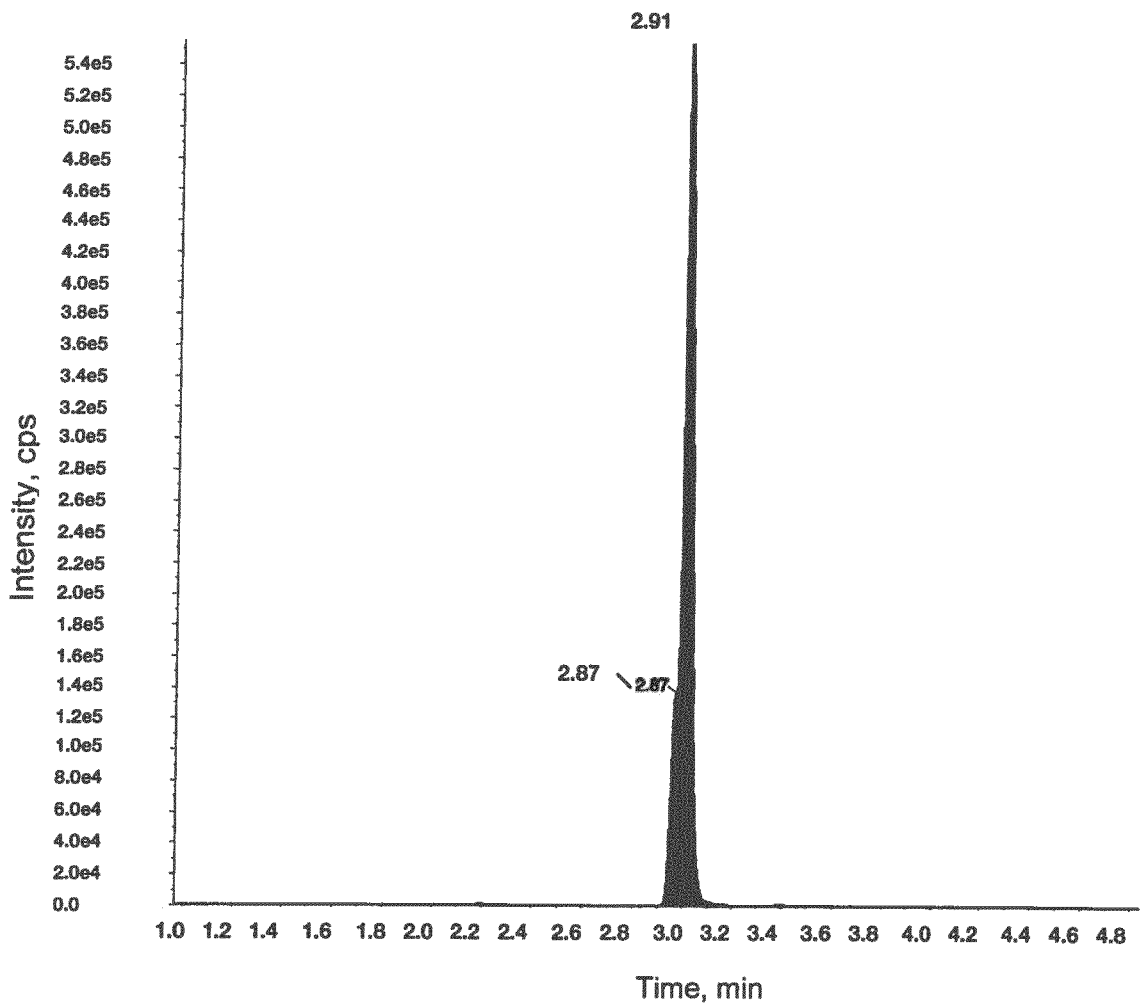

METHOD FOR THE DIAGNOSIS OF METACHROMATIC LEUKODYSTROPHY

CROSS-REFERENCE TO RELATED APPLICATIONS

This application is a 35 U.S.C. § 371 National Stage Entry of International Application No. PCT/EP2013/003750 having an international filing date of Dec. 11, 2013, which claims the benefit of European Application Nos. EP 12 008 257.3 filed Dec. 11, 2012, EP 12 008 0293.8 filed Dec. 12, 2012, and EP 13 001 454.1 filed Mar. 21, 2013, the content of each of the aforementioned applications is herein incorporated by reference in its entirety.

The present invention is related to a method for diagnosing metachromatic leukodystrophy, a method for determining the effectiveness of at least one treatment applied to a subject being positively tested for suffering from or being at risk of suffering from metachromatic leukodystrophy, a method for determining the effectiveness of a compound for the treatment of metachromatic leukodystrophy, the use of mass spectrometric analysis for the detection of a biomarker, and a kit for determining the presence of a biomarker in a sample from a subject.

Lysosomal storage diseases, also referred to herein as lysosomal storage disorders or LSDs, are a group of rare inherited metabolic disorders that result from defects in lysosomal function. LSDs result when a specific organelle in the body's cells—the lysosome—malfunctions. Some of the more prominent lysosomal storage diseases are Gaucher's disease and Fabry disease.

LSDs are caused by lysosomal dysfunction usually as a consequence of deficiency of a single enzyme required for the metabolism of lipids, glycoproteins or so-called mucopolysaccharides. Individually, LSDs occur with frequencies of about 1:10,000 to 1:250,000, however, as a group the incidence is about 1:5,000. Most of these disorders are autosomal recessively inherited; however, a few are X-linked inherited, such as Fabry disease and Hunter syndrome (MPS II).

Like other genetic diseases, individuals typically inherit lysosomal storage diseases from their parents. Although each disorder results from different gene mutations that translate into a deficiency in enzyme activity, they all share a common biochemical characteristic—nearly all lysosomal disorders originate from an abnormal accumulation of substances inside the lysosome.

Lysosomal storage diseases affect mostly children and they often die at a young and unpredictable age, many within a few months or years of birth. Many other children die of this disease following years of suffering from various symptoms of their particular disorder.

The symptoms of lysosomal storage disease vary, depending on the particular disorder and other variables like the age of onset, and can be mild to severe. They can include developmental delay, movement disorders, seizures, dementia, deafness and/or blindness. Some people with lysosomal storage disease have enlarged livers (hepatomegaly) and enlarged spleens (splenomegaly), pulmonary and cardiac problems, and bones that develop abnormally.

There are no causative cures for lysosomal storage diseases and treatment is mostly symptomatic, although bone marrow transplantation and enzyme replacement therapy (ERT) have been used for some indications with good success. In addition, umbilical cord blood transplantation is being performed at specialized centers for a number of these diseases. In addition, substrate reduction therapy (SRT), a method used to decrease the accumulation of storage material, is currently being evaluated for some of these diseases. Furthermore, chaperone therapy, a technique used to stabilize the defective enzymes produced by patients, is being examined for certain of these disorders. Gene therapy constitutes a further option for the treatment of these diseases.

Metachromatic leukodystrophy, also referred to herein as MLD or Arylsulfatase A deficiency, as used herein, is an LSD which is caused by a deficiency in lysosomal arylsulfatase A, also referred to herein as ARSA. ARSA catabolizes sulfatides (Von Figura et al, "Metachromatic leukodystrophy" In: Scriver C R et al. "The Metabolic and Molecular Bases of Inherited Disease" 8th edn). Sulfatides accumulate in multiple tissues including oligodendrocytes and Schwann cells, provoking demyelination in both the central and peripheral nervous system (Sedel et al., J Inherit Metab Dis., 2008 June).

To date a definitive diagnosis of MLD can only be made by measurement of ARSA activity on leukocytes together with genetic confirmation. Since numerous different mutations may be the cause of a particular lysosomal storage disease the sequencing of the lysosomal arylsulfatase A gene is applied in MLD in order to confirm the diagnosis.

Although there are attempts to apply diagnosis methods based on associated biochemical abnormalities there is an unmet need for a simple biochemical test exhibiting highly specific and highly sensitive detection of said lysosomal storage disease at an early stage, monitoring progression of the disease and early monitoring the efficacy of applied therapies.

Therefore, the identification of biomarkers for the early detection and diagnosis of MLD holds great promise to improve the clinical outcome of patients. It is especially important for patients with vague or no symptoms or to detect patients which fail to respond to a therapy.

A biomarker should be technically feasible in many hands, easy to measure; useful, with a consistent, relative magnitude between affected and controls, or treated and untreated; reliable, and accurate clinically, and classifiable as strongly predictive or prognostic.

Today, no biomarker for diagnosing MLD is available.

In Gaucher's disease, another LSD, some lysosomal enzymes, used as indirect biomarkers, were found to be elevated, including tartrate-resistant acid phosphatase, hexosaminidase, and a human chitinase, chitotriosidase. Thus there are attempts to monitor the reduction of storage cells in tissues by measurement of such surrogate markers of Gaucher cells like chitotriosidase and CCL18 (C. E. Hollak et al., J. Clin. Invest. 93 (1994) 1288-1292; R. G. Boot et al., Blood 103 (2004) 33-39). However, beside other disadvantages in the use of chitotriosidase as a biomarker for Gaucher's disease, said enzyme accumulates independent of a direct link to the pathology of Gaucher's disease. Furthermore, up to 35% of given ethnicities demonstrate a defect of the gene coding for chitotriosidase resulting in an artificially reduced or unmeasurable chitotriosidase activity.

The use of primary storage molecules as biomarker was assessed for glucosylceramide, in plasma of Gaucher's disease patients and compared to the level of glucosylceramide in healthy individuals (Groener et al. Biochim Biophys Acta. 2008 January-February; 1781(1-2):72-8. Epub 2007 Dec. 5; Plasma glucosylceramide and ceramide in type 1 Gaucher disease patients: correlations with disease severity and response to therapeutic intervention; Groener J E et al.). Nevertheless, although glucosylceramide measured in said study was increased in plasma of said patients, said increase of glucosylceramide was not prominent and thus the specificity and the sensitivity of the method were low showing that glucosylceramide is not applicable as a biomarker for Gaucher's disease.

Already in 1989 Rosengren et al. (lyso-sulfatide (galactosylsphingosine-3-O-sulfate) from metachromatic leukodystrophy and normal human brain, Rosengren B, Fredman P, Månsson J E, Svennerholm L.; J Neurochem. 1989 April; 52(4):1035-41.) showed that in lipidoses not only the catabolism of the major sphingolipid but also its lyso-compound is affected. Nevertheless, said study concluded that the lyso-compounds do not play a key role in the pathogenetic mechanisms in the sphingolipidoses. Thus, said lyso-compounds might not be suitable biomarkers for diagnosis of sphingolipidoses such as Gaucher's disease.

It is important to note that until today no use of a highly specific and highly sensitive biomarker and no method for the diagnosis of MLD is available beside the methods described above that exhibit an unsatisfactory limit of detection, sensitivity and/or specificity and thus proved to be unsuitable for clinical application.

Accordingly, there is need for a fast, simple and more importantly reliable method for the diagnosis of MLD.

In the light of the above, the problem underlying the present invention is to provide a method for the diagnosis of MLD.

It is a still further problem underlying the present invention to provide a method which allows to determine whether or not the subject is suffering from MLD or whether or not the subject is at risk of suffering from MLD.

A further problem underlying the present invention is to provide a method for determining the course and prognosis of MLD.

A still further problem underlying the present invention is to provide a method for determining rather quickly the effectiveness of at least one treatment applied to a subject being positively tested for suffering from or being at risk of developing MLD.

A further problem underlying the present invention is to provide a method for determining the effectiveness of a compound for the treatment of MLD.

Another problem underlying the present invention is to provide a biomarker which allows the specific and sensitive diagnosis of MLD.

A still further problem underlying the present invention is a kit which comprises a compound which interacts with a biomarker which is specific and sensitive for MLD.

Preferably, the biomarker of each and any problem underlying the present invention and the above problems in particular, is different from an enzyme, more preferably the biomarker is different from an enzyme selected form the group comprising arylsulfatase A, N-acetyl-alpha-glucosaminidase, arylsulfatase and beta-glucuronidase.

These and other problems are solved by the subject matter of the attached independent claims. Preferred embodiments may be taken from the attached dependent claims. Further aspects of the invention and various embodiments thereof are disclosed in the following. In particular, further aspects and embodiments are presented in the following and referred to as embodiment followed by a counter, i.e. "Embodiment 1" to "Embodiment 83", each and any thereof equally constitutes a solution to these and other problems.

Embodiment 1

A method for diagnosing metachromatic leukodystrophy in a subject comprising a step a), wherein the step a) comprises detecting a biomarker in a sample from the subject.

Embodiment 2

The method according to embodiment 1, wherein the method comprises
a step b) wherein the step b) comprises determining a level of the biomarker present in the sample.

Embodiment 3

The method according to any one of embodiments 1 or 2, wherein the level of the biomarker is indicative whether or not the subject is suffering from metachromatic leukodystrophy or whether or not the subject is at risk of suffering from metachromatic leukodystrophy.

Embodiment 4

The method according to any one of embodiments 1 to 3, wherein the sample from the subject is a sample from a subject who has previously been treated for metachromatic leukodystrophy or a sample from a subject who has previously been diagnosed for metachromatic leukodystrophy.

Embodiment 5

The method according to any one of embodiments 1 to 3, wherein the sample from the subject is a sample from a subject who has not previously been treated for metachromatic leukodystrophy or a sample from a subject who has not been previously diagnosed for metachromatic leukodystrophy.

Embodiment 6

The method according to any one of embodiments 1 to 5, wherein the method comprises
a step c), wherein the step c) comprises applying, maintaining, reducing, elevating or not applying a therapy based on whether the subject is suffering from metachromatic leukodystrophy or is at risk of suffering from metachromatic leukodystrophy.

Embodiment 7

The method according to any one of embodiments 1 to 6, wherein the method comprises
a step d), wherein the step d) comprises detecting the biomarker in a sample from the subject after a therapy has been applied, maintained, reduced, elevated or not applied in step c).

Embodiment 8

The method according to any one of embodiments 1 to 7, wherein the method comprises
a step e), wherein the step e) comprises determining a level of the biomarker in the sample from the subject after a therapy has been applied, maintained, reduced, elevated or not applied in step c).

Embodiment 9

The method according to embodiment 8, wherein the method comprises a step f), wherein the step f) comprises determining whether the level of the biomarker determined in step b) is lower than the level of the biomarker determined in step e).

Embodiment 10

The method according to embodiment 9, wherein the method comprises a step g), wherein the step g) comprises applying, maintaining, reducing, elevating or not applying a therapy based on step f).

Embodiment 11

The method according to any one of embodiments 1 to 10, wherein the biomarker is detected by means of immunoassay, mass spectrometric analysis, biochip array, functional nucleic acids and/or a fluorescent derivative of the biomarker.

Embodiment 12

The method according to embodiment 11, wherein the biomarker is detected by means of mass spectrometric analysis.

Embodiment 13

The method according to embodiment 12, wherein mass spectrometric analysis is selected from the group comprising SELDI, MALDI, MALDI-Q TOF, MS/MS, TOF-TOF and ESI-O-TOF.

Embodiment 14

The method according to embodiment 13, wherein the mass spectrometric analysis comprises or uses MS/MS.

Embodiment 15

The method according to any one of embodiments 1 to 14, wherein the method comprises protein precipitation and/or HPLC.

Embodiment 16

The method according to any one of embodiments 1 to 15, wherein the method comprises protein precipitation, HPLC and MS/MS.

Embodiment 17

The method according to any one of embodiments 1 to 16, wherein the subject is a human.

Embodiment 18

The method according to any one of embodiments 1 to 17, wherein step d) comprises detecting the biomarker in a sample comprises subjecting the sample to a protein precipitation step, precipitating protein from the sample, providing a supernatant of the sample, subjecting the supernatant of the sample to HPLC and MS/MS and determining the level of the biomarker that is present in the supernatant of the sample.

Embodiment 19

The method according to any one of embodiments 1 to 18, wherein the biomarker is free lyso-Gb1-sulfatide.

Embodiment 20

A method for diagnosing metachromatic leukodystrophy in a subject, wherein the method comprises the following steps:
i) adding an internal standard to a sample from the subject, wherein the sample from the subject is selected from the group comprising plasma, serum and blood;
ii) optionally mixing the sample containing the internal standard;
iii) subjecting the sample to a protein precipitation step, whereby protein from the sample is precipitated and a first supernatant of the sample is provided;
iv) optionally subjecting the first supernatant of the sample or at least a part thereof to a first separation step which provides a second supernatant, whereby preferably the first separation step is a step of centrifugation;
v) subjecting the first supernatant and/or the second supernatant, or at least a part thereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is preferably an HPLC column selected from the group comprising a C8 HPLC column and a C18 HPLC column, and wherein the second separation step provides a separated sample;
vi) subjecting the separated sample to MS/MS, wherein MS/MS comprises electrospray ionization and Multiple Reaction Monitoring;
and comprising
a step a), wherein the step a) comprises detecting a biomarker in a sample from the subject,
and optionally
a step b), wherein the step b) comprises determining a level of the biomarker present in the sample,
wherein the biomarker is free lyso-Gb1-sulfatide, and wherein the method is preferably a method according to any one of embodiments 1 to 19;

Embodiment 21

The method according to any one of embodiment 20, wherein the internal standard comprises lyso-Gb2.

Embodiment 22

The method according to any one of embodiments 1 to 21, wherein step b), step c) and/or step e) comprises comparing the level of the biomarker in the sample from the subject with a cut-off value.

Embodiment 23

The method according to any one of embodiments 1 to 22, preferably 22, wherein if the level of the biomarker in the sample from the subject is higher than the cut-off value this is indicative that the subject is suffering from metachromatic leukodystrophy or is at risk of suffering from metachromatic leukodystrophy.

Embodiment 24

The method according to any one of embodiments 1 to 22, preferably 22, wherein if the level of the biomarker in the sample from the subject is lower than the cut-off value this is indicative that the subject is not suffering from or is not at risk of suffering from metachromatic leukodystrophy.

Embodiment 25

The method according to any one of embodiments 1 to 24, wherein the cut-off value is such that a or the sensitivity for diagnosing metachromatic leukodystrophy in a subject is preferably from about 98.5% to 100%, more preferably 99,5% to 100%, and/or such that a or the specificity for diagnosing metachromatic leukodystrophy in a subject is from 99.4% to 100%, preferably 100%.

Embodiment 26

The method according to any one of embodiments 1 to 25, wherein step b) and/or step c) and/or step e) comprise(s) that a level of the biomarker in said subject is compared to a level of the biomarker detected in a sample from a control sample.

Embodiment 27

The method according to embodiment 26, wherein the control sample is a sample from a subject not having metachromatic leukodystrophy.

Embodiment 28

The method according to embodiment 26, wherein the control sample is a sample from a subject having metachromatic leukodystrophy carrier.

Embodiment 29

The method according to any one of embodiments 26 to 28, wherein if the level of the biomarker in the sample from the subject is higher than the level of the biomarker in the control sample this is indicative that the subject is suffering from and/or is at risk of suffering from metachromatic leukodystrophy.

Embodiment 30

The method according to any one of embodiments 1 to 29, preferably to embodiment 29, wherein the sample from the subject is selected from the group comprising blood, a blood product, urine, saliva, cerebrospinal fluid, stool, tissue sample and lymph.

Embodiment 31

The method according to embodiment 30, wherein the sample from the sample from the subject is selected from the group comprising blood and a blood product.

Embodiment 32

The method according to any one of embodiments 30 to 31, wherein the blood product is selected from the group comprising plasma, serum and dried blood.

Embodiment 33

The method according to any one of embodiments 1 to 32, preferably 32, wherein the method has a limit of determination for free lyso-Gb1-sulfatide of 0.05 ng/ml.

Embodiment 34

The method according to any one of embodiments 1 to 33, wherein the method is for the diagnosis of metachromatic leukodystrophy carrier and wherein the biomarker is free lyso-Gb1-sulfatide and the cut-off value is 0.05 ng/ml, and wherein the sample from the subject is preferably serum or plasma.

Embodiment 35

The method according to any one of embodiments 30 to 31, wherein the blood is whole blood, plasma, serum or dried blood, preferably plasma or serum.

Embodiment 36

The method according to embodiment 35, wherein the whole blood, plasma or serum is collected on a dry blood filter card.

Embodiment 37

A method for determining the course of metachromatic leukodystrophy in a subject, wherein the method comprises
a step a), wherein the step a) comprises determining at several points in time a level of a biomarker present in a sample from the subject.

Embodiment 38

The method according to embodiment 37, wherein the subject has been previously treated for metachromatic leukodystrophy and/or wherein the subject has been previously diagnosed for metachromatic leukodystrophy.

Embodiment 39

The method according to embodiment 37, wherein the subject has not been previously treated for metachromatic leukodystrophy and/or wherein the subject has not been previously diagnosed for metachromatic leukodystrophy.

Embodiment 40

The method according to any one of embodiments 37 to 39, wherein the method comprises
a step b), wherein the step b) comprises applying, maintaining, reducing, elevating or not applying a therapy based on whether the subject is suffering from metachromatic leukodystrophy or is at risk of suffering from metachromatic leukodystrophy.

Embodiment 41

The method according to any one of embodiments 37 to 40, wherein the method comprises a step c), wherein the step c) comprises detecting the biomarker in a sample from the subject after a therapy has been applied, maintained, reduced, elevated or not applied in step b).

Embodiment 42

The method according to any one of embodiments 37 to 41, wherein the method comprises
a step d), wherein the step d) comprises determining a level of the biomarker in the sample from the subject after a therapy has been applied, maintained, reduced, elevated or not applied in step b).

Embodiment 43

The method according to any one of embodiments 37 to 42, wherein the method comprises
a step e), wherein the step e) comprises determining whether the level of the biomarker determined in step a) is lower than the level of the biomarker determined in step d).

Embodiment 44

The method according to any embodiment 43, wherein the method comprises
a step f), wherein the step f) comprises applying, maintaining, reducing, elevating or not applying a therapy based on step e).

Embodiment 45

The method according to any one of embodiments 37 to 44, wherein the biomarker is free lyso-Gb1-sulfatide.

Embodiment 46

The method according to any one of embodiments 37 to 45, wherein the method comprises determining the level of free lyso-Gb1-sulfatide.

Embodiment 47

The method according to any one of embodiments 37 to 46, wherein the method comprises detecting free lyso-Gb1-sulfatide in the sample from the subject.

Embodiment 48

The method according to any one of embodiments 37 to 47, wherein the biomarker is detected by means of immunoassay, mass spectrometric analysis, biochip array, functional nucleic acids and/or a fluorescent derivative of the biomarker.

Embodiment 49

The method according to embodiment 48, wherein the biomarker is detected by means of mass spectrometric analysis.

Embodiment 50

The method according to embodiment 49, wherein mass spectrometric analysis is selected from the group consisting of SELDI, MALDI, MALDI-Q TOF, MS/MS, TOF-TOF and ESI-O-TOF.

Embodiment 51

The method according to embodiment 50, wherein the mass spectrometric analysis comprises or uses MS/MS.

Embodiment 52

The method according to any one of embodiments 37 to 51, wherein the method comprises protein precipitation and/or HPLC.

Embodiment 53

The method according to any one of embodiments 37 to 52, wherein the method comprises protein precipitation, HPLC and MS/MS.

Embodiment 54

The method according to any one of embodiments 37 to 53, wherein the subject is a human.

Embodiment 55

The method according to any one of embodiments 37 to 54, wherein step d) comprises detecting the biomarker in a sample comprises subjecting the sample to a protein precipitation step, precipitating protein from the sample, providing a supernatant of the sample, subjecting the supernatant of the sample to HPLC and MS/MS and determining the level of the biomarker that is present in the supernatant of the sample.

Embodiment 56

A method for determining the effectiveness of at least one treatment applied to a subject being positively tested for suffering from or being at risk of suffering from metachromatic leukodystrophy comprising
a step a), wherein the step a) comprises detecting at several points in time a level of a biomarker present in a sample from the subject.

Embodiment 57

The method according to embodiment 56, wherein the method comprises
a step b), wherein the step b) comprises determining at several points in time a level of a biomarker present in a sample from the subject.

Embodiment 58

The method according to any one of embodiments 56 or 57, wherein the biomarker is free lyso-Gb1-sulfatide.

Embodiment 59

The method according to any one of embodiments 56 to 58, wherein the subject has been previously treated for metachromatic leukodystrophy or diagnosed for metachromatic leukodystrophy.

Embodiment 60

The method according to any one of embodiments 56 to 58, wherein the subject has not been previously treated for metachromatic leukodystrophy or wherein the subject has not been previously diagnosed for metachromatic leukodystrophy.

Embodiment 61

The method according to any one of embodiments 56 to 60, wherein the method comprises a step d), wherein the step d) comprises applying, maintaining, reducing, elevating or not applying at least one treatment applied to the subject based on the decrease in the level of the biomarker as determined in step b).

Embodiment 62

The method according to any one of embodiments 56 to 61, wherein the method comprises a step e), wherein the step e) comprises detecting the biomarker in the sample from the subject, wherein the sample has been taken prior to the beginning of the treatment after applying, maintaining, reducing, elevating or not applying at least one treatment in step d) and, optionally determining a level of a biomarker present in a sample from the subject.

Embodiment 63

The method according to any one of embodiments 56 to 62, wherein the treatment is selected from the group comprising enzyme replacement therapy, substrate reduction therapy, chaperone therapy, gene therapy, stem cell transplantation of DNA/RNA skipping.

Embodiment 64

The method according to any one of embodiments 56 to 63, wherein the method comprises a step f), wherein the step f) comprises determining whether the level of the biomarker determined in step b) is lower than the level of the biomarker determined in step e).

Embodiment 65

The method according to embodiment 64, wherein the method comprises a step g) wherein step g) comprises applying, maintaining, reducing, elevating or not applying at least one treatment applied to the subject based on step f).

Embodiment 66

The method according to any one of embodiments 56 to 65, wherein the biomarker is detected by means of immunoassay, mass spectrometric analysis, biochip array, functional nucleic acids and/or a fluorescent derivative of the biomarker.

Embodiment 67

The method according to embodiment 66, wherein the biomarker is detected by means of mass spectrometric analysis.

Embodiment 68

The method according to embodiment 67, wherein mass spectrometric analysis is selected from the group consisting of SELDI, MALDI, MALDI-Q TOF, MS/MS, TOF-TOF and ESI-O-TOF.

Embodiment 69

The method according to embodiment 68, wherein the mass spectrometric analysis comprises or uses MS/MS.

Embodiment 70

The method according to any one of embodiments 56 to 69, wherein the method comprises protein precipitation and/or HPLC.

Embodiment 71

The method according to any one of embodiments 56 to 70, wherein the method comprises protein precipitation, HPLC and MS/MS.

Embodiment 72

The method according to any one of embodiments 56 to 71, wherein the subject is a human.

Embodiment 73

The method according to any one of embodiments 56 to 72, wherein the step of detecting the biomarker in the sample from the subject comprises precipitating protein from the sample from the subject, wherein precipitating protein from the sample provides a supernatant of the sample; subjecting a volume of the supernatant to HPLC and MS/MS and determining the level of the biomarker that is present in the sample from the subject.

Embodiment 74

A method of determining the effectiveness of a compound for the treatment of metachromatic leukodystrophy, wherein the method comprises the following steps:
  a) determining a level of a biomarker in a sample form a subject having metachromatic leukodystrophy;
  b) administering to said subject said compound;
  c) determining again the level of the biomarker in a sample from the subject after the compound has been administered to the subject; and
  d) determining whether the level of the biomarker determined in step c) is lower than the level of the biomarker determined in step a);
wherein if a level of the biomarker determined in step c) is lower than the level of the biomarker determined in step a) this indicates the effectiveness of said compound.

Embodiment 75

The method according to embodiment 74, wherein the biomarker is free lyso-Gb1-sulfatide.

Embodiment 76

The method according to any one of embodiments 74 to 75, wherein the method comprises determining a level of the biomarker in a control sample.

Embodiment 77

The method according to any one of embodiments 1 to 76, wherein the biomarker is free lyso-Gb1-sulfatide, wherein if the level of the biomarker in the sample from the subject is higher than the cut-off value of 0.05 ng/ml this is indicative that the subject is suffering from metachromatic leukodystrophy.

Embodiment 78

Use of mass spectrometric analysis for the detection of a biomarker, wherein the biomarker is free lyso-Gb1-sulfatide.

Embodiment 79

Use according to embodiment 78, wherein the detection comprises the use of HPLC.

Embodiment 80

Use according to any one of embodiments 78 to 79, wherein the mass spectrometric analysis comprises or uses MS/MS.

Embodiment 81

Use of a biomarker for the diagnosis of metachromatic leukodystrophy, preferably in a method according to any one of embodiments 1 to 77, wherein the biomarker is free lyso-Gb1-sulfatide.

Embodiment 82

A kit for determining the presence of a biomarker in a sample from a subject, wherein the kit comprises
a) an interaction partner of the biomarker;
b) optionally a solid support comprising at least one capture reagent attached thereto, wherein the capture reagent binds the biomarker; and
c) instructions for using the solid support to detect the biomarker,
wherein the biomarker is free lyso-Gb1-sulfatide.

Embodiment 83

The kit according to embodiment 82, wherein the kit is for
a) use in a method for diagnosing metachromatic leukodystrophy;
b) use in a method for determining the course of metachromatic leukodystrophy in a subject; and/or
c) use in a method for determining the effectiveness of at least one treatment applied to a subject,
wherein preferably the method of a), b) and/or c) is a method according to any one of embodiments 1 to 77.

It is within the present invention that the biomarker as used or referred to in connection with each and any aspect of the invention and each and any embodiment of the invention is preferably different from an enzyme, more preferably the biomarker is different from an enzyme selected form the group comprising arylsulfatase A, N-acetyl-alpha-glucosaminidase, arylsulfatase and beta-glucuronidase.

Preferably, the subject of each and any aspect of the invention and each and any embodiment of the invention is one suffering from a mutation selected form the group comprising the following MLD mutations

| | |
|---|---|
| c.465 + 1G > A | (5) |
| p.G309S | (4) |
| p.T393G | (3) |
| p.L113P | (2) |
| p.Q159X | (2) |
| p.D257E | (2) |
| p.K304R | (2) |
| p.G311S | (2) |
| p.R313Q | (2) |
| p.A316D | (2) |
| p.Y381fs | (2) |
| p.F387fs | (2) |
| p.H397Y | (2) |
| p.F400L | (2) |
| p.P426L | (2) |
| c.979 + 1G > A | (2) |
| p.P84L | (1) |
| p.S98F | (1) |
| p.G124S | (1) |
| p.G129R | (1) |
| p.C156Y | (1) |
| p.C158X | (1) |
| p.W195C | (1) |
| p.R246H | (1) |
| p.T276M | (1) |
| p.T306M | (1) |
| p.G309D | (1) |
| p.E314D | (1) |

These and other mutations are, for example, described in Pediatric Neurology, Part III: Handbook of Clinical Neurology, Eds. Olivier Dulac Maryse Lassonde Harvey B. Sarnat; Elsevier, 2013

The likelihood that the specific mutation is shown by an MLD patient is indicated in brackets in the above list.

The present inventors have surprisingly found that free lyso-Gb1-sulfatide, also referred to herein preferably as free lyso-glycocerebroside-sulfatide, constitutes a biomarker which allows for a method for diagnosing MLD in a subject, more specifically diagnosing MLD in a subject with high specificity and sensitivity using said free lyso-Gb1-sulfatide as the biomarker. Reliance on free lyso-Gb1-sulfatide as a biomarker in the diagnosis of MLD is superior over any method for the diagnosis of MLD based on an enzyme and arylsulfatase A in particular. Such superiority of a diagnosis based on free lyso-Gb1-sulfatide is shown in terms of both sensitivity and specificity. One of the reasons for the observed superiority of a free lyso-Gb1-sulfatide based diagnosis over an arylsulfatase A based diagnosis of MLD is the existence arylsulfatase A pseudodeficiencies, where a decrease in arylsulfatase A activity is—incorrectly—taken as an indication of MLD. Similar short-comings are observed in case of MLD diagnosis based on genetics: Some of the observed mutations of arylsulfatase A result in non-pathogenic pseudodeficiencies of arylsulfatase A.

The present inventors have also surprisingly found that free lyso-Gb1-sulfatide, which can be detected by the methods of the present invention, is circulating in the blood, and plasma and serum in particular, of a subject in a concentration of approximately 1/1000 of total Gb1-sulfatide. Moreover, the present inventors have surprisingly found that, unlike total Gb1-sulfatide, free lyso-Gb1-sulfatide which is present in the blood, and plasma and serum in particular, of a subject is useful in a method for diagnosing MLD in a subject comprising a step of detecting a biomarker in a sample from the subject, wherein the biomarker is free lyso-Gb1-sulfatide. The present inventors have also surprisingly found that the level of free lyso-Gb1-sulfatide determined in the sample from a subject by the methods of the present invention allows for diagnosing MLD with high sensitivity and high specificity.

In so far the present invention turns away from the teaching of the prior art in that the method of the present invention comprises determining the level of a lyso-compound and using said lyso-compound as a biomarker for diagnosis of a LSD. More specifically, the present inventors have surprisingly found that determining the level of free lyso-Gb1-sulfatide in a sample from a subject allows for diagnosing MLD with high sensitivity and high specificity.

It is also the merit of the present inventors of having recognized that a fraction of total Gb1-sulfatide which is accumulated in MLD, is present as a molecule in a free lyso form thereof, i.e. free lyso-Gb1-sulfatide, and is circulating in the blood, and plasma and serum in particular, of a subject in said free lyso form besides Gb1-sulfatide.

The term "lysosomal storage disorder", also referred to herein as "lysosomal storage disease" or "LSD", as preferably used herein, refers to genetic diseases and metabolic disorders that result from defects in lysosomal function. Lysosomal storage disorders are caused by lysosomal dysfunction usually as a consequence of deficiency of a single enzyme required for the metabolism of lipids, glycoproteins or so-called mucopolysaccharides. Like other genetic diseases, individuals inherit lysosomal storage diseases from their parents. Although each disorder results from different gene mutations that translate into a deficiency in enzyme activity, they all share a common biochemical characteristic—all lysosomal disorders originate from an abnormal accumulation of substances inside the lysosome.

MLD is an autosomal recessively inherited LSD which is commonly listed in the family of leukoencephalopathies. The term leukoencephalopathy means a disease or disorder that selectively or predominantly involves the white matter of the brain. It is associated with a group of diseases that affect the myelin itself, oligodendrocytes, astrocytes or even axons. The main acquired causes of leukoencephalopathies include inflammatory diseases, vascular diseases, infections, neoplasias and toxic causes (reviewed in Filley and Kleinschmidt-DeMasters, 2001, N Engl J Med). Hereditary leukoencephalopathies can be separated into three categories (Baumann and Turpin, 2000, J Neurol; Schiffmann and van der Knaap, 2004, Curr Opin Neurol; Sedel et al, 2005, Rev Neurol): (1) leukoencephalopathies characterized clinically, radiologically or pathologically but for which the gene causing the leukoencephalopathy is still unknown; (2) leukoencephalopathies caused by genes coding for proteins not directly involved in metabolic pathways and for which the diagnosis relies directly on gene analysis; and (3) leukoencephalopathies caused by genes coding for enzymes or proteins involved in the cell metabolism and for which the diagnosis relies mostly on biochemical analysis of plasma and urines samples. The third category corresponds to inborn errors of metabolism, also referred to herein as IEMs, which are important to recognize because specific treatments often exist (Sedel et al., 2007, Nat Clin Pract Neurol). Most IEMs causing leukoencephalopathies begin in childhood and have been described by neuropaediatricians. However, late-onset forms also exist that display different clinical and radiological features, sometimes very far from the classical paediatric description. With the exception of some leukoencephalopathies caused by certain lysosomal or peroxisomal disorders, neurologists are usually poorly familiar with IEMs.

MLD belongs to the third group of leukoencephalopathies, i.e. leukoencephalopathies caused by genes coding for enzymes or proteins involved in the cell metabolism. MLD is caused by a deficiency in lysosomal arylsulfatase A, also referred to herein as ARSA. ARSA catabolizes sulfatides (Von Figura et al, 2001, supra).

The incidence of the disease is around 1/100 000 and adult forms represent about 20% of cases. Clinical onset can be as late as the seventh decade of life (Bosch and Hart, 1978, Arch Neurol; Von Figura et al, 2001, supra). In adults, first symptoms are usually psychiatric, mimicking schizophrenia with delusion, hallucinations, disorganized behaviour and social dysfunction (Baumann et al 1991, Dev Neurosci). The clinical picture is completed after several years or decades by cognitive deficits as well as motor signs such as spastic paraparesis, cerebellar ataxia or mild demyelinating polyneuropathy. Motor onset forms of the disease are preferentially associated with the homozygous mutation P426L, whereas psychiatric forms are linked to the I179S mutation (Rauschka et al, 2006, Neurology). Magnetic Resonance Imaging shows a bilateral periventricular leukoencephalopathy with frontal predominance and cerebral atrophy. Importantly U-fibres are relatively spared at least at early stages of the disease (Sedel et al, 2001, supra).

To date, the only treatment which can be proposed is bone marrow transplantation, with few successes obtained in late-onset forms of the disease (Kidd et al., 1998, Arch Neurol).

Diagnosis of MLD according to the prior art is based on the measurement of ARSA activity on leukocytes. However, about 15% of people in Europe and the United States display low ARSA activity without clinical symptoms and no tissue or urine accumulation of sulfatides (Von Figura et al., 2001, supra). These pseudodeficiencies are caused by certain polymorphism within the ARSA coding gene (Von Figura et al., 2001, supra).

Thus the diagnosis of MLD in a patient with low ARSA activity according to the prior art requires the demonstration of high urinary excretion of sulfatides or molecular analysis of the ARSA gene.

Deficiency in saposin B, an activator necessary to activate sulfatides degradation, can cause MLD despite normal ARSA activity (Deconinck et al., 2007, Eur J Paediatr Neurol). Although such deficiency has not been described in adults to our knowledge, it should be suspected in patients with leukodystrophy and high urinary excretion of sulfatides.

Like many other genetic disorders that affect lipid metabolism, there are several forms of MLD, which are late infantile, juvenile, and adult.

In the late infantile form, which is the most common form of MLD (50-60%), affected children begin having difficulty walking after the first year of life, usually at 15-24 months. Symptoms include muscle wasting and weakness, muscle rigidity, developmental delays, progressive loss of vision leading to blindness, convulsions, impaired swallowing, paralysis, and dementia. Children may become comatose. Untreated, most children with this form of MLD die by age 5, often much sooner.

Children with the juvenile form of MLD (onset between 3 and 10 years of age) usually begin with impaired school performance, mental deterioration, and dementia and then develop symptoms similar to the late infantile form but with slower progression. Age of death is variable, but normally within 10 to 15 years of symptom onset although some juveniles can live for several decades or longer after onset.

The adult form commonly begins after age 16 as a psychiatric disorder or progressive dementia. Adult-onset MLD progresses more slowly than the late infantile and juvenile forms, with a protracted course of a decade or more.

Palliative care can help with many of the symptoms and usually improves quality and longevity of life.

That MLD is inherited in an autosomal recessive pattern means that both copies or both alleles of the gene must be mutated or altered in such a way that function is impaired, in contrast to a polymorphism, in which the nucleotide sequence is altered but causes no functional disruption, for a person to be affected by the disorder. Most often, the parents of a child with an autosomal recessive disorder are not affected but are carriers of one copy of the altered gene. Such carrier is referred to herein as MLD carrier. If both parents are carriers, there is a 25% chance with each pregnancy for an affected child. Genetic counseling and genetic testing is recommended for families who may be carriers of MLD.

Sulfatides accumulate in multiple tissues including oligodendrocytes and Schwann cells, provoking demyelination in both the central and peripheral nervous system (Sedel et al., supra). Sulfatides are a class of sulfated galactosylceramides synthesized primarily in the oligodendrocytes in the central nervous system. Sulfatides are a type of sulfolipid.

Gb1-sulfatide consists of a ceramide core, i.e. sphingosine bound to a fatty acid via an amide linkage and one glycosyl residue at the 1-hydroxyl moiety. A sulfate moiety is present at the $C_3$-atom of the glycosyl moiety. Preferably, the glycosyl moiety is either a galactosyl moiety or a glucosyl moiety. More preferably, the glycosyl moiety is a galactosyl moiety.

It will be understood by a person skilled in the art that the term "lyso-Gb1-sulfatide" as used herein, preferably in connection with the various methods of the invention, preferably means that the molecule is present in its free amino form. More precisely, lyso-Gb1-sulfatide as used herein, preferably differs from Gb1-sulfatide in that no fatty acid moiety is linked to the—primary—amino group of the sphingosine moiety of the molecule. Furthermore, lyso-Gb1-sulfatide is also referred to herein as glycosylsphingosine-sulfatide. In a preferred embodiment of the present invention, lyso-Gb1 sulfatide is of formula (I)

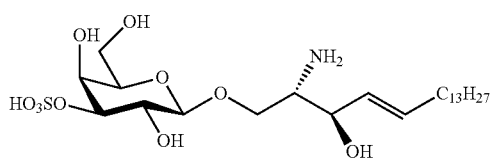

(I)

and is also referred to as lyso-Galactosyl-ceramide or lyso-galactosyl ceramide sulfatide or galactosyl sphingosine sulfatide.

It will be acknowledged by a person skilled in the art that depending on the analytical method used, it might not be possible to make a distinction whether a detected glycosyl-sphingosine-sulfatide contains a galactosyl moiety or a glucose moiety as the glycosyl moiety. Such a method is, for example, HPLC-MS/MS. Because of this, the term lyso-Gb1 sulfatide encompasses in its more general meaning as used herein galactosylsphingosine-sulfatide and/or glucosyl-sphingosine-sulfatide, whereby preferably the term lyso-Gb1 sulfatide means a compound of formula (I).

It will be understood by a person skilled in the art that the term "free lyso-Gb1-sulfatide" as used herein preferably refers to lyso-Gb1-sulfatide which is as such present in a sample from a or the subject, such as blood including dried blood or plasma or serum, and, preferably, is not the result of a manipulation of the sample of said subject. Such manipulation of a sample can be the one described by Groener et al. (Groener et al., Biochimica et Biophysica Acta 1781(2908)72-78, 2007). In accordance therewith, free lyso-Gb1-sulfatide which is present as such in the blood including dried blood or plasma or serum of a subject from whom the sample is taken, is more particularly not a lyso-Gb1-sulfatide which is generated by chemical, biochemical or physical treatment of the sample contained in the blood sample, plasma sample and/or serum sample, preferably outside of the body of the patient. Preferably, free lyso-Gb1-sulfatide is not a lyso-Gb1-sulfatide prepared by chemical treatment of free lyso-Gb1-sulfatide as contained in a sample of a subject, whereby the sample is preferably a sample selected from the group consisting of plasma, serum and blood including dried blood. More preferably, free lyso-Gb1-sulfatide as used herein is different from lyso-Gb1-sulfatide prepared by Toda K. et al (Toda K. et al., (1989) Biochemical and Biophysical Research Communications, Vol. 159, No. 2, pp 605-611); in other words, Toda K et al. prepared by means of chemical treatment of lyso-Gb1-sulfatide free lyso-Gb1-sulfatide without recognizing that such free lyso-Gb1-sulfatide, although in a much lower amount, was already present in the sample and more specifically a blood sample including plasma sample serum sample and dried blood sample; by subjecting lyso-Gb1-sulfatide to said chemical treatment, the amount of free lyso-Gb1-sulfatide already present in the sample as such, was obscured.

From the above it is evident that both Toda K et al. and Groener et al. followed the same strategy in terms of derivatization. It will be also understood by a person skilled in the art that free lyso-Gb1-sulfatide as used herein, preferably is present in addition to Gb1-sulfatide and is a compound produced by the subject's metabolic activities. Accordingly, Gb1-sulfatide, which is the molecule that is accumulated in connection with MLD is present in the sample from the subject and has compared to the molecule in a free lyso form, i.e. free-lyso-Gb1-sulfatide, present in the blood, and plasma and/or the serum of the subject at least a fatty acid moiety linked to the—primary—amino group of the sphingosine moiety of lyso-Gb1-sulfatide.

In an embodiment of the biomarker according to the present invention the biomarker is detected by means of immunoassay, mass spectrometric analysis, biochip array, functional nucleic acids and/or a fluorescent derivative of the biomarker. In connection therewith it is important to note that such detection allows for the selective detection of the biomarker as present in the blood of a subject as such and particularly is not the result of a manipulation of the sample of said subject resulting in a change of the concentration of the biomarker, such as the derivatization of Gb1 into lyso-Gb1 according to the method of the prior art as described above. Such manipulation may result in the inability to distinguish the biomarker which is present in its free-lyso-form from the substance which is the result of said manipulation, for example the result of said derivatization. Thus the biomarker of the present invention cannot be detected as such and the level of said biomarker cannot be determined as such, respectively, without detecting the manipulated further substance, e.g. Gb1 converted into lyso-Gb1 according to the method of the prior art. In the light thereof it will be immediately understood that the biomarker present in the blood of the subject such as free-lyso-Gb1-sulfatide present as such in the blood of the subject, is also present in the sample of the subject as such and may, nevertheless, be selectively labeled with and/or linked to a means such as a fluorescent dye or a nucleic acid molecule specifically binding the biomarker. Such selective labeling or linking allows detecting and/or determining the level of the labeled or linked biomarker, without labeling of, linking to or converting a further substance, such as the converted lyso-Gb1 of the prior art, which cannot be distinguished from the biomarker, more precisely the labeled or linked biomarker. In connection therewith, e.g. a fluorescent derivative of the biomarker of the present invention concerns a biomarker which is labeled with and/or bound to a fluorescence dye or molecule, i.e. resulting in a fluorescent derivative of the biomarker, which allows for detecting the fluorescent derivative and/or determining the level of the fluorescent derivative of the biomarker of the invention.

The term "sample" as used herein means preferably a limited quantity of a subject's material, wherein said subject's material is part of or has been taken from a subject and/or a subject's body. Preferably, said material is selected from the group comprising body fluids such as blood, a blood product such as preferably plasma, serum, urine, saliva, cerebrospinal fluid and lymph, as well as stool or any kind of tissue and or cell material being part of a subject and/or a subject's body. A particular preferred sample is a serum sample or a plasma sample which is used or for use in any of the methods of the invention. A further preferred sample is a dried blood sample. It will be acknowledged by a person skilled in the art, that the presence of and/or a level of a biomarker of the invention in said sample is intended to be similar to and represent the presence and/or the level of the biomarker in a larger amount of that subject's material. More precisely and as an illustrative, non-limiting example, a level of a biomarker of the invention determined in a sample of, e.g., some ml of blood from a subject also represents a level of said biomarker in the blood of the subject's body. Furthermore, in an embodiment of the method of the invention for diagnosing MLD in a subject, a sample from the subject comprises said subject's material in a form, for example processed, fixed and/or preserved such that said sample is suitable for use in the method of the invention, whereby such processing, fixing and/or preserving preferably does not generate lyso-Gb1-sulfatide which was not as such present in the blood of the patient. The subject's material in the sample may thus be diluted, for example with a solvent suitable for the method of the invention such as methanol and/or water, may be dried, for example on a filter card, may be resolved after having been dried such, for example with a solvent suitable for the method of the invention such as methanol and/or water, or a substance may be added, wherein said substance prevents blood from coagulation such as for example EDTA, citrate or heparin. It will be further understood by a person skilled in the art that the method of the invention comprises that said subject's material is separated into single components of said subject's material and/or single components of said subject's material are extracted from said subject's material, for example blood is separated into plasma or serum and cellular blood components or protein is precipitated from the sample. Accordingly, in an embodiment of the method according to the present invention wherein the method comprises protein precipitation and/or HPLC, precipitation of protein preferably results in a) a precipitation of cellular blood components and/or protein, more preferably forming a pellet after a step of centrifugation, and b) the biomarker being not precipitated and being present in the supernatant after a step of centrifugation. A person skilled in the art will immediately understand that in an embodiment of the method according to the present invention wherein the method comprises HPLC a supernatant containing the biomarker(s) of the present invention or a part thereof is subjected to HPLC. In connection therewith it is important to understand that the supernatant or a part thereof which is subjected to HPLC comprises the biomarker to be detected as well as, preferably, an internal standard. In an embodiment of the method of the invention wherein an internal standard is added to the sample, the internal standard may be added to the sample before or after a precipitation step, i.e. the internal standard may be added into the sample immediately after the sample is taken from the subject or after thawing of the sample such as the blood, plasma or serum before analysis, or may be added to the supernatant which is subjected to HPLC, as well as in between these time points. A person skilled in the art will know, how and when an internal standard is preferably added to the sample in order to achieve an accurate detection and determination of a level of the biomarker. It is within the present invention that the terms "dry blood" and "dried blood" are preferably used in an interchangeable manner, it not explicitly indicated to the contrary.

It will be immediately understood that after such processing, fixing and/or preserving the sample is subjected to the methods of the invention for detecting and/or determining the level of a biomarker contained in said sample whereby such processing, fixing and/or preserving preferably does not generate lyso-Gb1-sulfatide which was not present in the sample from the patient as such.

In an embodiment of the method of the present invention wherein whole blood is collected on a dry blood filter card preferably approximately 50 to 200 µl of full blood, plasma or serum are collected on a spot of said dry blood filter card having a diameter of 3 mm. A person skilled in the art will acknowledge that the exact volume thus collected may vary depending on the hematocrit of the specific patient.

The levels of glucosylceramide and its precursor ceramide were used in the prior art to correlate their presence in plasma with the severity of Gaucher's disease type I and the response to the application of therapy (Groener et al., Biochimica et Biophysica Acta 1781(2908)72-78, 2007). Thereby, the level of lyso glucosylceramide was found to be different although ceramide levels were not significantly different in the plasma of treated and untreated Gaucher's disease type I patients.

In the study reported by Groener et al. (Groener et al., supra) the ratio of glucosylceramide/ceramide was used to discriminate between Gaucher's disease patients and healthy patients. glucosylceramide and ceramide were measured with high performance liquid chromatography (HPLC) essentially as described in Groener et al. (J. E. M. Groener et al., Clin. Chem. 53 (2007) 742-747). In connection therewith it is important to understand that glucosylceramide present in the plasma mainly consists of a sugar moiety and a ceramide moiety. The ceramide moiety comprising a sphingosine and a fatty acid moiety. According to the method of the prior art lipids are extracted and ceramide and glucosylceramide are deacetylated by alkaline hydrolysis thus forming the lyso form, i.e. lyso-glucosylceramide (T. Taketomi et al., J. Biochem. (Tokyo) 120 (1996) 573-579). Subsequently, the thus produced lyso-glucosylceramide is labeled with a fluorescence dye by derivatization with 0-phthaldialdehyde (OPA) at the primary amine group. Afterwards the derivatized sphingoid bases were separated by reverse phase HPLC and detected with a fluorescence detector. Thus said method of the prior art is able to detect total glucosylceramide consisting of free lyso-glucosylceramide and glucosylceramide and is not able to distinguish a level of free lyso-glucosylceramide from a level of glucosylceramide in a sample from a subject. The level of said total glucosylceramide after cleavage of the various fatty acid moieties from the $NH_2$-group of the glucosylceramide is usually in a range of from 5 to 30 µg per mL plasma or serum. From this it is evident that in the method of Groener et al. (Groener et al., supra) the total glucosylceramide which can be prepared and obtained, respectively, from a sample, preferably a blood sample, from a subject is used as a biomarker rather than the free lyso-glucosylceramide contained in the blood and accordingly also in the sample without performing a cleavage of the fatty acid moiety/moieties, preferably a cleavage performed by an operator handling the sample. Insofar, the present invention is related to the detection of free lyso-Gb1-sulfatide rather than total-Gb1-sulfatide.

Although total glucosylceramide measured as lyso-glucosylceramide in said study of the prior art was increased in plasma of said patients, said increase in total glucosylceramide was not prominent and thus the specificity and the sensitivity of the method were low showing that glucosylceramide is not suitable as a biomarker for Gaucher's disease.

It is an embodiment of the methods of the present invention comprising detecting and/or determining the level of free lyso-Gb1-sulfatide in a sample from a subject that free lyso-Gb1-sulfatide and/or the level of free lyso-Gb1-sulfatide is determined separate from and/or apart from Gb1-sulfatide or a level of Gb1-sulfatide which may be present in the blood of a subject. In a further embodiment Gb1-sulfatide and/or a level of Gb1-sulfatide is detected/determined in addition to the detection of and/or the determining of a level of free lyso-Gb1-sulfatide.

Importantly, each primary amine circulating in the plasma and being sufficiently lipophilic to be extracted concomitantly with Gb1-sulfatide using an organic solvent according to said method of the prior art is labeled accordingly and is thus able to disturb the detection of cleaved lyso-Gb1-sulfatide.

In an embodiment of the biomarker according to the present invention what has been outlined above with regard to free lyso-Gb1-sulfatide also applies to any biomarker of the present invention being present as in a free-lyso form.

Insofar, the biomarker of the present invention and uses thereof clearly exceed the performance of methods for diagnosing MLD known the prior art, more specifically, attempts of such methods using biomarkers. It will be immediately understood that a method for diagnosing MLD in accordance with Toda K et al. (Toda K et al., supra) and thus analogous to the method applied by Groener et al. for diagnosing Gaucher's disease (Groener et al., supra) is prejudicial compared to the methods of the present invention in that diagnosing of MLD based on such method of the prior art using total Gb1-sulfatide rather than free lyso-Gb 1-sulfatide as the method of the prior art using total glucosylceramide rather than free lyso-glucosylceramide is not suitable for reliable clinical application thereof, i.e. the method has no sensitivity and specificity sufficient to diagnose Gaucher's disease by a reliable statistically secured prediction.

In clear contrast thereto the present invention provides methods for the diagnosis of MLD and biomarkers used in said methods which allow the diagnosis of MLD with high sensitivity and high specificity.

The term "MLD status", also referred to herein as "MLD status", preferably refers to the status of the disease in the subject. Examples of types of MLD statuses include, but are not limited to, the subject's risk of suffering or developing MLD, the stage of the disease in a subject and the effectiveness of treatment of the disease. Other statuses and degrees of each status are known in the art. In an embodiment of the present invention the MLD status comprises a severe, mild, or healthy MLD status.

The term "diagnosing" as preferably used herein, means determining the presence or the absence of a disease or disorder in a subject and/or determining whether a subject is at risk for developing a disease, a disorder or symptoms related to a disease or disorder as well as predicting a status of a disease. "Diagnosis" or "diagnosing" as used herein also preferably means that a cause of symptoms of a disease which are present or will be present is identified.

In connection therewith it is important to note that a person skilled in the art, such as a skilled clinician consulted by a subject suffering from symptoms or suspected to be ill, applies the methods of the present invention and thus determines whether a subject is at risk for developing a disease, particularly MLD, whether a subject suffers from such disease or predicts the status of such disease, preferably based on the result obtained by the practicing of the methods of the present invention.

Based on said diagnosis the person skilled in the art will recommend to apply, maintain, reduce, elevate or not apply a therapy or to perform further diagnostic tests.

It is thus an embodiment of the method of the present invention for diagnosing MLD that the method comprises giving a recommendation whether a therapy should be applied, maintained, reduced, elevated or not applied.

The term "detecting" in the context of the present invention preferably means a method which includes detecting the presence or absence of a substance in a sample and/or qualifying the type of said substance. Detecting can be accomplished by methods known in the art and those further described herein, including, but not limited to, the direct measurement of the affected protein(s) e.g. the sequencing of the gene coding for ARSA. Any suitable method can be used to detect one or more of the biomarkers described herein. These methods include, without limitation, mass spectrometry (e.g. HPLC-MS/MS), fluorescence (e.g. sandwich immunoassay), HPLC-fluorescence or HPLC-UV preferably after derivatization of free lyso-Gb1-sulfatide.

A biomarker as preferably used herein, is any biological compound, such as a protein and a fragment thereof, a peptide, a polypeptide, a proteoglycan, a glycoprotein, a lipoprotein, a carbohydrate, a lipid, a nucleic acid, an organic or inorganic chemical, a natural polymer, and a small molecule, which is differentially present in a sample from a subject of one phenotypic status (e.g. having a disease) as compared with another phenotypic status (e.g. not having the disease) and which may be isolated from, or measured in the sample from the subject. Furthermore, the biomarker can be the entire intact molecule, or it can be a portion thereof which is preferably detected by mass spectrometric analysis, an antibody, another protein specifically binding the biomarker, functional nucleic acids specifically binding the biomarker and/or a fluorescent label. A biomarker is furthermore considered to be informative if a measurable aspect of the biomarker is associated with a given status of the patient, such as a particular status of MLD. Such a measurable aspect may include, for example, the presence, absence, or the level of the biomarker in the sample from the subject and/or its presence as part of a profile of biomarkers. A measurable aspect may also be a ratio of two or more measurable aspects of biomarkers, which biomarkers may or may not be of known identity, for example. A profile of biomarkers comprises at least two such measurable aspects, where the measurable aspects can correspond to the same or different classes of biomarkers such as, for example, a nucleic acid and a carbohydrate. A biomarker profile may also comprise at least three, four, five, 10, 20, 30 or more measurable aspects. In one embodiment, a biomarker profile comprises hundreds, or even thousands, of measurable aspects. In another embodiment, the biomarker profile comprises at least one measurable aspect of at least one biomarker and at least one measurable aspect of at least one internal standard.

In an embodiment of the method according to the present invention an internal standard is added to a sample from a subject. It will be acknowledged that by said addition of internal standard, also referred to herein as IS, to the sample, i.e. spiking of the sample, to be subjected to the method according to the present invention, the concentration of IS in the sample is known and, e.g., by determining the area under the peak, i.e. the peak area, of the internal standard in, e.g., an HPLC-mass spectrometric chromatogram the relation between a peak area and a concentration of a substance, e.g. of IS and/or the biomarker of the present invention, e.g. free lyso-Gb1-sulfatide, can thus be calculated, e.g., by calculating the ratio of the peak area of free lyso-Gb1-sulfatide and the peak area of IS. A person skilled in the art will further acknowledge that various molecules may be used as an IS. Nevertheless an IS having a similar chemical structure or an isotopically labeled lyso-Gb1-sulfatide compared to the molecule such as the biomarker, e.g. free lyso-Gb1-sulfatide, is preferable. In accordance therewith, the present inventors have in an embodiment chosen lyso-Gb2 which is not present as such in nature in concentrations which could influence the precise determination of lyso-Gb1-sulfatide. In a preferred embodiment the molecule being the IS can be distinguished from the biomarker or the biomarkers of the present invention, e.g. free lyso-Gb1-sulfatide, in the method of the present invention. In a further preferred embodiment the IS is selected such that a molecule which is ideally not present or rare in nature. In an embodiment of the present invention where the internal standard is added to a sample from a subject, it is preferred that the IS is added such that it is dissolved in a solvent, e.g. ethanol, prior to said addition to the sample. In a further preferred embodiment that the solvent is selected such that said solvent is capable of causing protein precipitation, preferably is capable of causing the protein precipitation step as subject to the method of the present invention.

In some embodiments of the present invention a protein precipitation and/or protein precipitation step is part of the method of the present invention. It will be understood that precipitation as used herein, preferably means the formation of a solid in a solution, i.e. for example the formation of a protein precipitate in a sample, e.g. serum, from a subject. When precipitation, e.g. protein precipitation, occurs in a sample, the solid formed is called the precipitate, or when compacted by a centrifuge, a pellet. The liquid remaining above the solid is in either case called the supernatant. The present invention contemplates different methods of precipitation and/or separating said supernatant and said precipitate or pellet, comprising, among others, settling or sedimentation and centrifugation. A person skilled in the art will know further methods for protein precipitation and/or for separating a supernatant and a protein precipitate, nevertheless said skilled person will acknowledge that if a method, preferably a method of the invention, is applied were precipitated protein will disable a device such as a column or HPLC-column used in connection with the present invention the precipitated protein is preferably separated from the solvent and/or the sample.

In some embodiments of the present invention a level of a biomarker of the present invention, e.g. free lyso-Gb1-sulfatide, determined by a method of the present invention in a sample is compared to a level of the same or another biomarker of the present invention determined by a method of the present invention in another sample, e.g. from the same patient, from another patient, from a control and/or from the same or different time points, and/or a cut-off value, and/or a level of a control and/or a level of an IS. In connection therewith "comparing" or "compared to" as used herein, preferably means the mathematical comparison of the two or more values of the levels of the biomarker(s). It will thus be immediately evident whether one of said values is higher, lower or identical if at least two of such values are compared with each other.

The term "cut-off value" as preferably used herein refers to a level, concentration and/or a titer of a biomarker of the present invention, more preferably a level range, concentration range and/or titer range of the biomarker.

In one particular embodiment thereof
using free lyso-Gb1-sulfatide as the biomarker allows for
diagnosing MLD using a cut-off value for free lyso-Gb1-sulfatide of 0.05 ng/ml plasma or serum.
In a further particular embodiment thereof using free lyso-Gb1-sulfatide as the biomarker allows for
diagnosing MLD using a cut-off value for free lyso-Gb1-sulfatide of 0.05 ng/ml plasma or serum with a sensitivity of 100% and a specificity of 100%.

In some embodiments of the present invention the level of the biomarker is also determined in a control. As used herein, a control is preferably a sample from a subject wherein the MLD status of said subject is known. In an embodiment a control is a sample of a healthy patient. In a further embodiment an amount of said biomarker is added to said sample of a healthy patient prior to determining the level of said biomarker in said sample of a healthy patient comprising said added biomarker with a method of the present invention. In a further embodiment the control is a sample from at least one subject having a known MLD status, such known MLD status comprising severe, mild, or healthy MLD status, e.g. a control patient. In a further preferred embodiment the MLD status also comprises the genetic status with regard to mutations of the gene or genes, affected in said disease, comprising the gene coding for ARSA, i.e. comprising the subject having homozygous and/or compound heterozygous mutations, the subject being a carrier of a mutation.

In a further preferred embodiment the control is a sample from a subject not being treated for MLD. In a still further preferred embodiment the control is a sample from a single subject or a pool of samples from different subjects and/or samples taken from the subject(s) at different time points.

The term "level" or "level of a biomarker" as used herein, preferably means the concentration of a substance and/or titer of a substance, preferably of a biomarker of the invention and more preferably of free lyso-Gb1-sulfatide, within a sample of a subject. It will be understood by a skilled person that in certain embodiments said sample is not necessarily subjected to a method of the invention as a non-processed sample, the method comprising determining a level of said biomarker, i.e. said sample may be subjected, e.g. to a step of protein precipitation, separation, e.g. centrifugation and/or HPLC and subsequently subjected to a step of determining the level of the biomarker, e.g. using mass spectrometric analysis. It should be further noted that whenever the term "a" level of a biomarker is used in connection with a level of the biomarker of the invention which is to be determined according to the present invention, "the" level of the biomarker of the present invention which is to be determined by the methods of to the present invention and which is contained in the sample subjected to the method(s) of the invention is meant. A preferred sample is either a blood sample, a serum sample or a plasma sample.

The level of a biomarker is different between different statuses of MLD if the mean or median level of the biomarker in the different groups is calculated to be statistically significant. Common tests for statistical significance include, among others, t-test, ANOVA, Wilcoxon, Mann-Whitney, odds ratio and Kruskal-Wallis. Biomarkers, alone or in combination, provide measures of relative risk that a subject belongs to one phenotypic status or another. Therefore, biomarkers of the present invention are useful in an embodiment of the present invention as markers for disease, therapeutic effectiveness of a drug or a treatment.

The term "determining the level" of a biomarker as used herein, preferably means methods which include quantifying an amount of at least one substance in a sample from a subject and/or quantifying an amount of said substance contained in a part of the body of the subject, such as saliva, blood, lymph, serum, plasma or liquor and/or quantifying an amount of said substance in the subject, the substance being selected from the group comprising a biomarker.

It will be understood by a person skilled in the art that detecting and/or determining the level of free lyso-Gb1-sulfatide in a sample from the subject, thus preferably comprises that Gb1-sulfatide present in the blood of a subject is not chemically converted, transformed or derivatized such that free lyso-Gb1-sulfatide cannot be detected and/or the level thereof cannot be determined separate from and/or apart from Gb1-sulfatide. The person skilled in the art will acknowledge that Gb1-sulfatide present in a sample from a subject which is subjected to a step of deacylation, e.g. by hydrolysis in methanolic sodium hydroxide, will result in cleavage of the fatty acid moiety from the Gb1-sulfatide and thus will undesirably result in a chemically converted, transformed or derivatized form of Gb1-sulfatide which cannot be differentiated from free lyso-Gb1-sulfatide. It is thus the merit of the present inventors to recognize that free lyso-Gb1-sulfatide apart from Gb1-sulfatide is useful in a method for diagnosing MLD.

In a preferred embodiment of the methods of the present invention the method is for detecting and/or determining the level of free lyso-Gb1-sulfatide in a sample from a subject, wherein Gb1-sulfatide present in the sample from the subject is not subjected to a step resulting in deacylation of Gb1-sulfatide, preferably is not subjected to a step resulting in cleavage off of a fatty acid moiety from the Gb1-sulfatide contained in the sample. In a further preferred embodiment of the method of the present invention Gb1-sulfatide present in the sample from the subject is not chemically converted, transformed or derivatized. In a still further preferred embodiment of the method of the present invention free lyso-Gb1-sulfatide present in the sample from the subject is separated from Gb1-sulfatide present in the sample from the subject prior to a step that would result in cleavage of a fatty acid moiety from the Gb1-sulfatide and/or prior to a step in which Gb1-sulfatide is chemically converted, transformed or derivatized. In a still further preferred embodiment a step of detecting and/or determining the level of a biomarker in a sample from the subject, wherein the biomarker is free lyso-Gb1-sulfatide, is performed subsequent to separation using HPLC by application of mass spectrometric analysis.

In an embodiment of the methods of the invention a subject will be considered to be healthy regarding MLD if it has no mutation of the functional parts of the gene coding for ARSA and/or no mutation of the gene coding for ARSA resulting in a reduction of or deficiency of the respective protein or the activity thereof, resulting in symptoms associated with MLD.

A subject is considered to be a healthy subject with regard to MLD if the subject does not suffer from symptoms associated with MLD. Moreover in an embodiment of the methods of the invention a subject will be considered to be healthy regarding MLD if it has no mutation of the functional parts of the gene coding for ARSA and/or no mutation of the gene coding for ARSA resulting in a reduction of or deficiency of the respective proteins or the activity thereof, resulting in symptoms associated with MLD.

In connection therewith it is important to understand that a patient being a carrier of a mutation as outlined above is not considered to be a healthy subject within the meaning of the present invention although said carrier may not suffer from symptoms associated with MLD. In certain embodiments of the methods of the present invention MLD also comprises MLD carrier. It is important to note that the methods of the invention are equally suitable to identify an MLD carrier. The methods of the present invention are suitable to diagnose whether or whether not a subject is an MLD carrier. The method of the present invention is further suitable for differentiating, diagnosing and/or differentially diagnosing whether a subject is healthy, is an MLD carrier or is an MLD patient.

Said mutations, i.e. mutations of the gene encoding ARSA, will be detected if a sample from the subject is subjected to a genetic testing for such mutations as described herein. In a further embodiment of the present invention a sample from a healthy subject is used as a control sample or as a blank matrix in the methods of the present invention. A blank matrix as used herein is preferably a sample from a healthy subject. Nevertheless it will be understood that such a blank matrix may contain a native level of free lyso-Gb1-sulfatide.

In an embodiment of the present invention the level of a biomarker is indicative for the subject for suffering from or for being at risk for developing a disease or disorder. The level of the biomarker determined by the method according to the present invention is compared to a control level of the biomarker, wherein the result of said comparison allows for diagnosing a disease.

More specifically, comparing the level of the biomarker in the sample from the subject to the control level of the biomarker comprises comparing the level of the biomarker in the sample from the subject to a cut-off value, wherein if a level of the biomarker in the sample from the subject is higher than the cut-off value, this is indicative that the subject is suffering from or is at risk for developing MLD; and/or wherein if a level of the biomarker in the sample from the subject is lower compared to the cut-off value this is indicative that the subject is not suffering from or is not at risk for developing MLD.

The term "being at risk for developing a disease" as used herein preferably means that it is likely that a subject suffer from said disease and/or will develop said disease or symptoms associated with said disease, particularly if no treatment is applied. In connection therewith it has to be acknowledged that LSDs are genetic disorders and thus the occurrence of relatives, particularly parents having said disease or having a mutation known to be the cause of said disease are indicative for a subject, e.g. the child of two MLD patients, to be at risk for developing said disease. It will be furthermore acknowledged that the progression of a disease is linked to the occurrence of symptoms as well as the severity of said symptoms. Accordingly, a person not suffering from symptoms at present, however, may be at risk for developing the disease, for example, because although genetically mutations of a gene, known to cause a disease are present, no symptoms or no severe symptoms occur. Nevertheless, it will be immediately understood that the methods and biomarkers of the present invention, particularly if the level(s) of said biomarker(s) according to the present invention are elevated, allow for diagnosing that such subject is at risk for developing the disease independent from the presence or absence of symptoms. Accordingly, the methods according to the present invention allows for determining whether a subject is at risk of suffering from MLD. It is also within the present invention that a therapy is applied, maintained, reduced, elevated or not applied based on whether the subject is at risk of suffering from MLD or not.

It is also within the present invention that comparing the level of the biomarker in the sample from the subject to a control level allows for determining the severity of MLD, wherein if a level of the biomarker in the sample from the subject is within the cut-off value that is indicative that the subject is suffering from or is at risk for developing MLD of a more severe status or progression; and wherein if a level of the biomarker in the sample from the subject is lower or higher compared to the control level, i.e. the cut-off value, that is indicative that the subject is not suffering from or is not at risk for developing MLD of a less severe status or progression. In a further embodiment of the present invention that comparing the level of the biomarker in the sample from the subject to the control level comprises comparing a level of the biomarker in said subject to a level of the biomarker detected in a sample from a control, wherein if a level of the biomarker in the sample from the subject is elevated, increased or higher compared to the control sample this is indicative that the subject is suffering from and/or is at risk for developing MLD; and/or a level of the biomarker in the sample from the subject is elevated, increased or higher compared to the control sample this is indicative that the subject is suffering from or is at risk for developing MLD of a more severe status or progression. Said control preferably is selected from the group comprising healthy subjects, subjects suffering from MLD or being at risk of suffering from MLD symptoms, subjects being positively tested for a mutation or a combination of mutations of the gene coding for ARSA, wherein the mutation or the combination of mutations of the gene coding for ARSA are indicative for a perspective of the subject to develop MLD of a more severe or less severe status or progression. In a further embodiment of the present invention that a control level is determined in a sample from a control, wherein optionally free lyso-Gb1-sulfatide is added to the sample from the control in a specific quantity prior to determining the level of free lyso-Gb1-sulfatide in the sample from the control.

It is the merit of the present inventors that a method for diagnosing MLD in a subject could be established wherein the method comprises detecting a biomarker in a sample from a subject, wherein the biomarker is free lyso-Gb1-sulfatide, preferably further comprising determining a level of the biomarker in the sample from the subject, and more preferably further comprising comparing the level of the biomarker in the sample from the subject to a cut-off value, which shows high sensitivity, i.e. a sensitivity of at least 99.0%, 99.1%, 99.2%, 99.3%, 99.4%, 99.5%, 99.6%, 99.7%, 99.8%, 99.9% or 100%. In other words the sensitivity, which means the proportion of actual positives which are correctly identified as such is high, which means that the percentage of MLD patients correctly identified as having the disease is as high as has been outlined above. In contrast, in a statistic test as described herein specificity means the proportion of negatives which are correctly identified as negatives, in other words the percentage of healthy patients correctly identified as not having MLD. A person skilled in the art will acknowledge that thus an optimal prediction of a diagnostic test such as in some embodiments of the methods according to the present invention in general aims to achieve 100% sensitivity, i.e. predict all patients having a disease, such as MLD or being at risk of suffering from said disease, as having the disease or being at risk from suffering from said disease, respectively. Such sensitivity can be achieved with the cut-off value for free lyso-Gb1-sulfatide being 0.05 ng/ml plasma or serum.

In an embodiment of the methods according to the present invention a specificity of at least 80.0%, 85.0%, 90.0%, 95.0%, 97.5%, 99.0%, 99.1%, 99.2%, 99.3%, 99.4%, 99.5%, 99.6%, 99.7%, 99.8%, 99.9% or 100% is preferred. In a further embodiment of the present invention of the methods according to the present invention the methods allow for diagnosing MLD in a subject independent from a progression status of MLD in the subject. Such specificity can be achieved with the cut-off value for free lyso-Gb1-sulfatide being 0.05 ng/ml plasma or serum.

More specifically, the methods of the present invention allow for diagnosing MLD in a subject having an early status of MLD as well as in a subject having an advanced or progressed status of MLD.

The power of a method to correctly diagnose MLD is commonly measured as the sensitivity of the method, the specificity of the method or the area under a receiver operated characteristic curve (also referred to herein as "ROC curve"). An ROC curve is a plot of the true positive rate against the false positive rate for the different possible cut-off values of a diagnostic method. An ROC curve shows the relationship between sensitivity and specificity. Sensitivity is the percentage of true positives that are predicted by a test to be positive, while specificity is the percentage of true negatives that are predicted by a test to be negative. An ROC-curve provides the sensitivity of a test as a function of 1-specificity. The greater the area under the ROC-curve the more powerful the predictive value of the test. Accordingly, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. Therefore, the area under the ROC is a measure of test accuracy. The accuracy of the test depends on how well the test separates the group being tested into those with and without the disease in question. An area under the curve (also referred to herein as "AUC") of 1 represents a perfect method, while an area of 0.5 represents a less useful method. Thus, preferred diagnostic methods of the present invention have an AUC greater then 0.50, more preferred methods have an AUC greater than 0.9 and most preferred methods have an AUC greater than 0.99.

Other useful and suitable measures for the utility of a method are positive predictive value and negative predictive value. A positive predictive value is the percentage of actual positives that test as positive. A negative predictive value is the percentage of actual negatives that test as negative.

A person skilled in the art will acknowledge that although the specificity and/or the sensitivity of the methods according to the present invention are as high as described above and were determined as described in the Examples hereinafter, individual cases may not be excluded where a patient having MLD will be tested false negative or where a patient not having MLD will be tested false positive with a method of the invention. A person skilled in the art will thus immediately acknowledge that according to the methods according to the present invention, wherein a level of a biomarker is compared to a cut-off value and wherein said comparison to said cut-off value is for use to diagnose a disease such as MLD, said cut-off value represents a level of said biomarker which discriminates a particularly disease status from another, e.g. which discriminates a level of a biomarker indicative that the subject has MLD from a level of a biomarker indicative that the subject is an MLD carrier, and/or from a level and/or a value in a healthy subject. Having said this, it is obvious for the person skilled in the art that also according to the methods of the present invention, wherein the method is for diagnosing MLD individual cases may not be excluded where a patient having MLD will be tested false negative or where a patient not having MLD will be tested false positive, or where the type and/or status is diagnosed incorrectly with a method of the invention.

Taking said cases into account while determining the specificity and the sensitivity of the method according to the present invention, the specificity and the sensitivity will be lower than the above described values. Nevertheless, the person skilled in the art will also acknowledge that such high specificity and such high sensitivity as has been outlined above has never been described before for a method for diagnosing MLD. Therefore it is important to note that although the sensitivity and the specificity of the method of the present invention may vary if patient collectives other than the one reported in the Example part, e.g. varying in number of patients, will are subject to the methods of the present invention, it is the firm belief of the inventors that no method known in the prior art using, especially using biomarkers will achieve a higher specificity and a higher sensitivity compared to the methods according to the present invention. This is especially true since the limit of detection of the methods of the present invention allows for determining the level of free lyso-Gb1-sulfatide in healthy subjects. Accordingly, a diseased subject tested false negative applying the methods of the present invention is tested false negative for the reason that a level of the biomarker in a sample from said false negative tested diseased subject is as high as the level of the biomarker in a sample from a healthy subject. In particular it is important to note that said false negative tested subject is not tested negative for the reason that the level of the biomarker was too low to be determined by the method of the present invention.

A "limit of detection" or "limit of determination"—both terms are used herein in a synonymous manner—of a substance such as free lyso-Gb1-sulfatide, as used herein, preferably is a level of the substance determined by a method for determining a level of the substance, wherein a level less then or lower then said limit of detection cannot be determined by said method. It is thus immediately clear that a "cut-off value" and a "limit of detection", as used herein, are preferably not necessarily identical, although both reflect a certain level of a substance, e.g. of a biomarker of the present invention. It will be immediately understood that in contrast to a cut-off value will be selected preferably such that selectivity and sensitivity of the method are as high as possible. In contrast thereto a limit of detection represents an absolute level of the biomarker of the present invention which reflects the minimum level of biomarker which can be detected with a method for determining the level of said biomarker. It is thus immediately clear that a limit of detection depends on the method for determining a level of a substance and on the substance the level of which is to be determined by the method. A skilled person will immediately understand that a high limit of detection, e.g. higher than an ideal cut-off value would possibly result in a low sensitivity of the method since the percentage of true positives that are predicted by a test to be positive also depends on whether a level of the biomarker may be determined for said true positives. In other words, if the limit of detection is higher than an ideal cut-off value, true positives having a level of the biomarker slightly higher than the cut-off value may not be distinguished from true negatives having a level of the biomarker lower than the cut-off value since no level of the biomarker may be determined for both true positives having a level of the biomarker slightly higher than the cut-off value and negatives having a level of the biomarker lower than the cut-off value. It is thus immediately clear that a low limit of detection is of advantage. It is therefore also the merit of the inventors to show that a lower limit of detection allows for a method for diagnosing MLD in a subject comprising a step of determining a level of a biomarker present in the sample with higher selectivity and sensitivity. An "ideal cut-off value" as used herein, preferably is the cut-off value as described herein the method using said ideal cut-off value has the highest selectivity and sensitivity.

It is an embodiment of the methods according to the present invention to comprise a step of validating said method by diagnosing a disease or disorder, preferably MLD in a subject by the method of the present invention; a step of diagnosing the disease or disorder, preferably MLD, in a subject by a genetic testing, comprising sequencing of a gene, preferably sequencing of a gene a mutation of which is known to the one skilled in the art to cause the disease or disorder, more preferably sequencing the gene coding for ARSA in case of MLD; and comparing the results of said method and said genetic testing. A healthy subject as used herein, preferably is considered to be healthy with regard to a disease or disorder if said subject is not suffering from symptoms associated with said disease or disorder and if the result of a genetic testing reveals no mutations of a gene a mutation of which is known to the one skilled in the art to cause the disease or disorder. A healthy subject also is understood to be a subject being positively tested for not having MLD. In a preferred embodiment a healthy subject is a subject not being a carrier of MLD.

The term "qualifying MLD status" in a subject as used herein, preferably means a classification of a subject's biomarker profile selected from the group comprising to identify or detect the presence or absence of MLD in the subject, to predict the onset of or the risk for developing of MLD in the subject, to determine the course of MLD in a subject, to determine and/or predict the severity of MLD in a subject, to determine whether a subject suffers from an early status of MLD or an advanced or progressed status of MLD or to determine whether a level of a biomarker in a subject has significantly changed over time.

The term "managing subject treatment" or "subject management" as used herein, preferably refers to the behavior of the clinician or physician subsequent to the determination of MLD status. For example, if the result of the method according to the present invention is inconclusive or there is reason that confirmation of status is necessary, the physician may order new tests, such as testing for the function of the affected proteins and/or sequencing of the gene coding for ARSA. Alternatively, if the status indicates that treating for MLD is appropriate, the physician may schedule the subject for treating for MLD. Likewise, if the status is negative or if the results show that treatment has been successful, no further management may be necessary. Nevertheless a person skilled in the art will immediately acknowledge that besides gene therapy any therapy applied has to be applied lifelong to an MLD patient. Furthermore it is an embodiment of the present invention that managing subject treatment comprises titrating of a dose of a drug applied as a treatment for MLD, e.g. units of recombinant enzyme applied in ERT, administered to a patient. In some embodiments of the methods of the present invention wherein a level of a biomarker present in a sample from a subject is determined at several points in time, or is compared to other levels of the biomarker, a cut-off value and/or a level of said biomarker in a control, a skilled person will apply or not apply a therapy, or amend a therapy already applied in order to treat or not to treat, or to continue treating MLD.

It is within the present invention that a skilled person will apply a dosage and/or maintain a dosage or amend a dosage, e.g. apply a dosage or a higher dosage, i.e. elevate a dosage, if such a comparison of the level of a biomarker shows e.g. that the level of said biomarker is higher than for example, a cut-off value, i.e. the patient is diagnosed to have MLD; or that a level determined in the same patient earlier in time is lower or the same, i.e. a therapy applied is not sufficient, i.e. does not result in a decrease in the level. On the other hand skilled person will apply or not apply a dosage or maintain or reduce a dosage, e.g. apply no dosage or a lower dosage, i.e. decrease a dosage, if such a comparison of the level of a biomarker shows e.g. that the level of said biomarker is lower than for example, a cut-off value, i.e. the patient is diagnosed not to have MLD disease; or that a level determined in the same patient earlier in time is higher, i.e. a therapy applied is sufficient, i.e. does result in a decrease in the level. In an embodiment of the present invention a relatively high level of free lyso-Gb1-sulfatide based on such a comparison is indicative for applying a high dosage of recombinant enzyme applied in ERT and/or a relatively low level of free lyso-Gb1 based on such a comparison is indicative for applying a low dosage of recombinant enzyme applied in ERT. Nevertheless it will also be immediately understood that a skilled person will consider a patient's history, i.e. a skilled person managing subject treatment of a patient suffering from MLD and being treated such that a level of biomarker is lower than a cut-off value, for example, will not decide to stop treatment rather than decrease a dosage and increase the time between further applications of the methods of the present invention.

The course of MLD may be determined by the method according to the present invention by determining a level of the biomarker in the sample from the subject at different time points in the course of the disease. It is important to note that a single application of a method for diagnosing MLD according to the present invention allows for diagnosing MLD and in certain embodiments comprises a step of managing subject treatment based on the diagnosis of whether the subject is suffering from or for being at risk for developing MLD. If a subject a sample of which is thus subjected to the method of the present invention is tested positive for suffering from or to be at risk for developing MLD a skilled clinician will know how to decide concerning managing subject treatment, i.e. how the subject will be treated, e.g. applying a certain dose of enzyme in relation to an ERT. It will be immediately understood that independent of the decision of a skilled clinician on how to manage subject treatment the skilled clinician may decide for at least one additional application of the method according to the present invention on a later time point. It is thus an embodiment of the present invention that the levels of the biomarker determined at the different time points, wherein different time points means at least two time points, may be compared. Without wishing to be bound by any theory the present inventors have found that the level of the biomarker of the present invention in samples form one particular patient may be correlated to the severity of the disease in said patient at the time point the sample from the patient is taken. It will be thus immediately understood that an elevated level of the biomarker determined in the sample of a later time point compared to the level of the biomarker determined in the sample of an earlier time point is indicative for a more severe status of the subject at the later time point compared to the status of the subject at the earlier time point. A decreased level of the biomarker determined in the sample of a later time point compared to the level of the biomarker determined in the sample of an earlier time point is indicative for a less severe status of the subject at the later time point compared to the status of the subject at the earlier time point. Accordingly, in one aspect the present invention provides a method for determining the course of MLD in a subject comprising the step of determining at several points in time a level of a biomarker present in a sample from the subject, wherein the biomarker is free lyso-Gb1-sulfatide. In a further aspect the invention concerns a method for determining the effectiveness of at least one treatment applied to a subject being positively tested for suffering from or being at risk for developing MLD comprising the step of determining at several points in time a level of a biomarker present in a sample from the subject, wherein the biomarker is free lyso-Gb1-sulfatide. It will be immediately understood by a person skilled in the art that the methods of the present invention thus allow for selecting a therapy and/or adjusting the doses and/or dosage of a selected therapy based on the results of the method of the invention. If for example the subject is scheduled for treating for MLD the method for diagnosing MLD in a subject according to the present invention may be applied every 3 months and levels of the biomarker thus determined will be compared in order to determine the effectiveness of the treatment(s) and/or therapy/therapies applied to the subject. If the subject reaches a status, wherein a stable level of the biomarker is maintained over time the frequency of application of the method for diagnosing MLD in a subject according to the present invention may be reduced to every 6 month. If the dosage of the therapy is changed, e.g. the units of recombinant enzyme applied in ERT are reduced or increased, the frequency of application of the method for diagnosing MLD in a subject according to the present invention may be set back to every 3 month. By comparison of the determined levels of the biomarker in the samples from the subject the skilled physician will recognize whether the level of the biomarker increases, decreases or whether a stable level of the biomarker is maintained over time. Accordingly, the skilled physician may decide to reduce the dosage of the therapy, e.g. the units of recombinant enzyme applied in ERT; to increase the dosage of the therapy; or to maintain the dosage of the therapy according to the comparison of the levels of the biomarker determined with the method according to the present invention. A significant reduction of the level of free lyso-Gb1-sulfatide within a period of 12 month is indicative for a successful therapy for MLD, wherein reduction as used herein, preferably means that the level of free lyso-Gb1-sulfatide determined by the method of the present invention determined at the end of a time period is compared to the level of free lyso-Gb1-sulfatide determined by the method of the present invention determined at the beginning of said time period. Accordingly the skilled physician may decide to reduce the dosage of the applied therapy or to maintain the dosage of the therapy. If the reduction of the level of free lyso-Gb1-sulfatide is significantly weaker the skilled physician may decide to increase the dosage of the therapy. It is also a merit of the present inventors to have recognized that the reduction of the level of free lyso-Gb1-sulfatide correlates with the effectiveness of a therapy. The stronger the reduction of the level of the free lyso-Gb1-sulfatide within a time period, e.g. 12 months, the more successful is a therapy, such as for example ERT, SRT or a chaperone based therapy. It is thus a further embodiment of the present invention that the method of the present invention is for comparing the effectiveness of a therapy or of at least two therapies applied to a subject.

A person skilled in the art thus will acknowledge that the progression, i.e. course of MLD, as well as the effectiveness of a therapy in a single subject can be monitored by frequent determining of the level of free lyso-Gb1-sulfatide in samples from the subject.

In a further aspect the invention concerns a method for determining the effectiveness of at least one treatment applied to a subject being positively tested for suffering from or being at risk for developing MLD comprising the step of determining at several points in time a level of a biomarker present in a sample from the subject, wherein the biomarker is free lyso-Gb1-sulfatide. In connection with what has been outlined above in relation to managing subject treatment a person skilled in the art will immediately understand that the effectiveness of one treatment or the combination of at least two treatments may be compared applying the methods of the present invention. Thus it is possible to test and compare several new drugs, dosage forms, dosages or treatments for MLD by the method of the present invention.

It is an embodiment of the present invention that the method for diagnosing MLD according to the present invention is independent of whether the subject has or has not been previously treated for MLD. Thus the sample from the subject may be a sample from a subject who has been previously treated for MLD as well as a sample from a subject who has not been previously treated for MLD. It is thus a further embodiment of the present invention that the method of the present invention comprises a step of managing subject treatment and/or determining a level of the biomarker in the sample from the subject after subject management. Said subject treatment can be based on the diagnosis of whether the subject is suffering from or for being at risk for developing MLD; on the detection of the biomarker in a sample from the subject after subject management; or on the determining of the level of the biomarker in the sample from the subject after subject management. Nevertheless a person skilled in the art will understand that a sample of some patients not having MLD or of some patients being successfully treated for MLD will show a level of free lyso-Gb1-sulfatide lower than the limit of detection.

Without wishing to be bound by any theory the present inventors assume that the level of free lyso-Gb1-sulfatide present in a sample from a subject further correlates with the severity of the disease in a subject suffering from MLD. In connection therewith the present inventors found by evaluating the results provided herein (e.g. shown in FIG. 2 herein) assume that although, in principle, the level of free lyso-Gb1-sulfatide is different in particular individuals, and more specifically may be different in particular individuals having the same mutation(s), that the higher is a level of free lyso-Gb1-sulfatide, the higher is the severity of a course of MLD in terms of a statistical mean according to a clinical score. Thereby the level of free lyso-Gb1-sulfatide correlates with the severity of MLD in that in patients being positively tested for distinct mutations of the gene coding for ARSA being known to generally causes a mild or a more severe course of MLD, a level of free lyso-Gb1-sulfatide determined in said patients statistically correlates with the severity generally related to such mutation.

Thus a further embodiment of the different aspects of the present invention concerns a method for determining the severity of MLD in a subject comprising a step of
a) determining a level of the biomarker present in a sample from the subject wherein the biomarker is free lyso-Gb1-sulfatide and a step of
b) determining the severity of MLD, e.g. by comparing the level of free lyso-Gb1-sulfatide in a subject preferably determined by a method of the present invention to a clinical score.

In connection therewith it is important to note that if a level of free lyso-Gb1-sulfatide is determined in samples from the patients suffering from MLD showing the L444 Pa mutation usually linked to a more severe course of MLD upon sequencing of the respective gene (homozygous and compound heterozygous) subjected to a method of the present invention a mean-level of free lyso-Gb1-sulfatide is higher than the mean-level of the free lyso-Gb1-sulfatide determined in samples from the patients suffering from MLD showing a mutation usually linked to a more mild course of MLD upon sequencing of the respective gene, applying the same method. A "mutation usually linked to a more severe course of MLD" as used herein preferably is known to cause a more severe course of MLD—this is especially true in case the subject is homozygous as to said mutation. Corresponding to that in an embodiment a higher mean-level of free lyso-Gb1-sulfatide is determined in the homozygous compared to the homozygous mutation usually linked to a milder course of MLD. Moreover patients having a compound heterozygous usually linked to a more severe course of MLD have a significantly lower free lyso-Gb1-sulfatide level, than homozygous ones. A person skilled in the art will know clinical scores to categorize the severity of MLD or symptoms or an entirety of symptoms thereof. It is thus an embodiment of the method of the present invention that the course of MLD in a patient is predicted and more particularly the severity of MLD is determined based on the level of the biomarker determined according to the method of the present invention.

A person skilled in the art will acknowledge that a level of the biomarker of the present invention determined in a sample from a subject wherein said level of the biomarker is correlated with the severity of MLD as described above, will be indicative for applying a certain therapy and/or dose or dosage of said therapy. For example, if the level of the biomarker determined according to the methods of the invention is correlated with "severe" MLD status the subject is scheduled for treatment of MLD and the method for diagnosing MLD in a subject according to the present invention may be applied every 3 months and levels of the biomarker thus determined will be compared in order to determine the effectiveness of the treatment(s) and/or therapy/therapies applied to the subject. If the subject reaches a status, wherein the level of the biomarker is correlated with a "mild" MLD or wherein a stable level of the biomarker is maintained over time the frequency of application of the method for diagnosing MLD in a subject according to the present invention may be reduced to every 6 month.

In another aspect the present invention is related to a method of determining the effectiveness of a composition for the treatment of MLD. Such method may comprise the steps of determining a level of free lyso-Gb1-sulfatide in a subject having MLD; administering to said subject said compound in an amount sufficient to determine the effectiveness of said compound; re-determining the level of free lyso-Gb1-sulfatide in said subject; comparing the level of free lyso-Gb1-sulfatide determined before and after administering said composition, wherein a lower level of free lyso-Gb1-sulfatide determined after administering said composition compared to the level of free lyso-Gb1-sulfatide determined after administering said composition indicates the effectiveness of said compound for treating MLD.

MLD affects mostly children and they often die at a young and unpredictable age, many within a few months or years of birth. Many other children die of this disease following years of suffering from various symptoms of their disorder.

A preferable biomarker for the diagnosis of MLD would allow for diagnosis of MLD with high sensitivity and high specificity independent from the age of the subject.

It is the merit of the present inventors having found that the biomarkers of the present invention are useful for the diagnosis of MLD in a subject independent from the age of the subject. It is thus an embodiment of the present invention that the method of the present invention allows for diagnosing MLD in a subject independent from age, preferably under the provio that the subject is at least 2 months old. In a preferred embodiment the method of the present invention the subject is a subject of young age. A subject of young age as used herein preferably is a subject of less than 30 years of age, more preferably of less than 20 years of age and most preferably of less than 10 years of age.

It will be acknowledged by a person skilled in the art that the sensitivity and specificity of the diagnostic method of the invention, i.e. the proportion of actual positives which are correctly identified, depends at least to a certain extent on the patient group tested. In connection with the instant invention and the various methods of the invention, a patient or subject is preferably a human of at least 2 months age.

It is within the invention that the methods of the invention and in particular the method of the invention for diagnosing metachromatic leucodystrophy is one for diagnosing juvenile form of metachromatic leucodystrophy and/or adult form of metachromatic leucodystrophy.

It will also be acknowledged by a person skilled in the art that the cut-off value for free lyso-Gb1-sulfatide of 0.05 ng/ml plasma or serum is one which is preferably applied in case the limit of determination, which is also referred to herein as limit of detection, of the analytical method used in determining the level or concentration of free lyso-Gb1-sulfatide is 0.05 ng free lyso-Gb1-sulfatide/ml plasma or serum, or in case the limit of determination of the analytical method used in determining the level or concentration of free lyso-Gb1-sulfatide is set to 0.05 ng free lyso-Gb1-sulfatide/ml plasma or serum.

The present invention is now further illustrated by the following figures and examples from which further features, embodiments and advantages may be taken.

More specifically,

FIG. 1A is an HPLC-mass spectrometric chromatogram displaying peak intensity of free lyso-Gb1-sulfatide and IS of a healthy subject (upper chromatogram for free lyso-Gb1-sulfatide and lower chromatogram for the internal standard);

FIG. 1B is an HPLC-mass spectrometric chromatogram displaying peak intensity of free lyso-Gb1-sulfatide and IS of subject diagnosed as MLD-positive (upper chromatogram for free lyso-Gb1-sulfatide and lower chromatogram for the internal standard);

Figure 4:
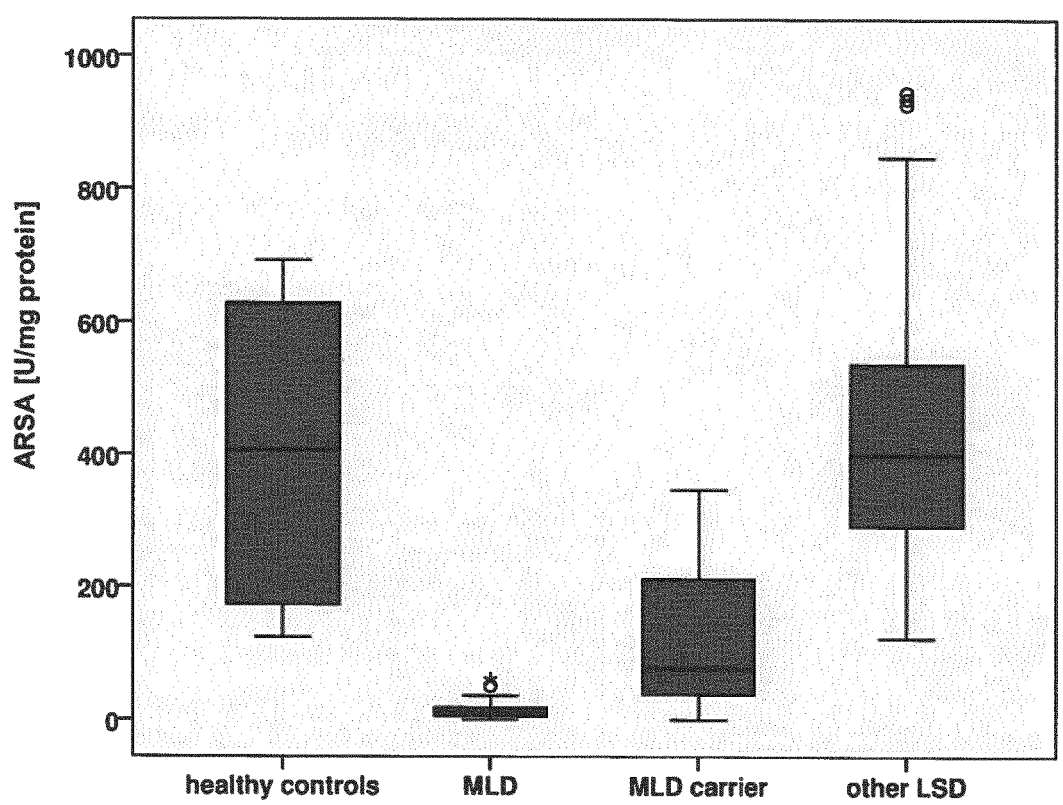
Figure 5:
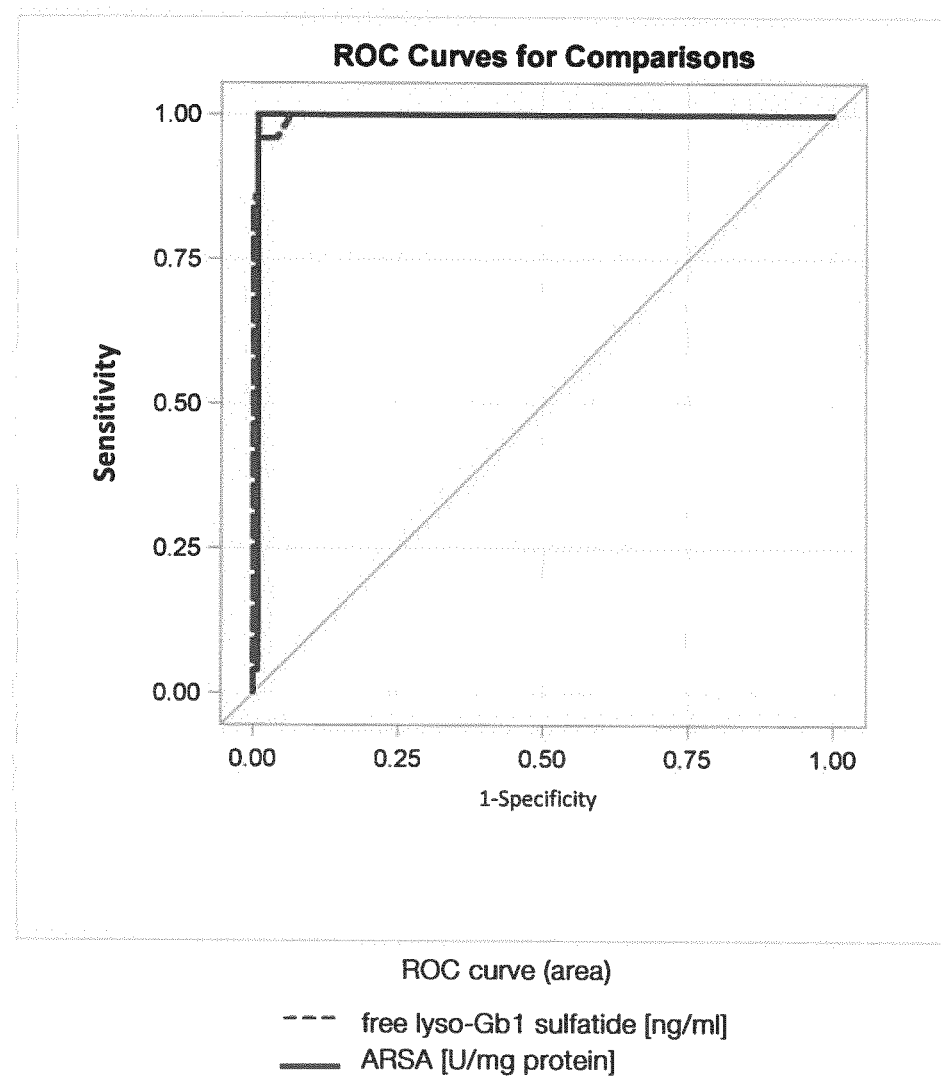

FIG. 4 is a boxplot indicating levels of enzymatic arylsulfatase A activity in U/mg protein in the second cohort of MLD diagnosed subjects compared to the levels in subjects positively diagnosed as suffering from other LSDs, in subjects positively diagnosed as being MLD carrier, and in subjects being healthy controls; and FIG. 5 is a graph showing receiver operating characteristics (ROC) for the diagnosis of MLD.

EXAMPLES

In the Examples described in the following human plasma or serum was used as a sample from a subject. Nevertheless a person skilled in the art will acknowledge that depending on the used type of sample from a subject, e.g. comprising saliva, liquor, plasma, serum, full blood, blood on a dry blood filter card or another blood product, the method of the present invention has to be adjusted to the type of sample and furthermore a cut-off value has to be determined for each type of sample according to the method described in the following examples. The present inventors have found that using a sample of human serum in the method as described below instead of a sample of human plasma will lead to identical results in terms of the level of free lyso-Gb1-sulfatide, if the sample of human serum and the sample of human plasma are taken from the same subject, at the same time point, and if the samples were measured in parallel; and, more particularly, will lead to the same cut-off value.

Example 1: Method for the Detection of Free Lyso-Gb1-Sulfatide in Human Plasma/Serum Equipment For detecting free lyso-Gb1-sulfatide in a sample of plasma from a subject the following equipment was used.

| Apparatus/Piece of Equipment | Type/Producer |
|---|---|
| HPLC pump | Series 200, Perkin Elmer, USA |
| Sample injector | Series 200, Perkin Elmer, USA |
| Column oven | Series 200, Perkin Elmer, USA |
| Mass selective detector | API 5000, AB SCIEX, USA/Canada |
| Multi-tube vortexer DVX-2500 | Henry Troemner LLC, USA |
| Vortex mixer | Vortex Genie 2; Scientific Industries, USA |
| Centrifuge | Megafuge 1.0; Heraeus, Germany |
| Multipette(s), pipette(s) | Eppendorf, Germany |
| Water bath | SW21-C, Julabo, Germany |

Reagents

For detecting free lyso-Gb1-sulfatide in a sample of plasma from a subject the following reagents were used.

To that extent that values depend on temperature (e.g. the pH value) such values were determined at a temperature of 25° C.

| Reagent | Purity |
|---|---|
| Acetonitrile (ACN) | HPLC-grade or Gradient grade |
| Acetone | 99.5% |
| Formic acid (FA) | p.a., 98-100% |
| Methanol (MeOH) | Gradient (LiChrosolv) |
| Trifluoroacetic acid (TFA) | purum > 98% |
| Water | ASTM-I |

The abbreviation "p.a." as used herein means "pro analysis".
The term "purum" as used herein, preferably means a commercial grade of a chemical compound having a purity of the above specified value.
ASTM-I as used herein refers to a water grade standard purity achieved by purification methods comprising Reverse Osmosis and Ultraviolet (UV) Oxidation.

Preparation of Calibration Standards

A lyso-Gb1-sulfatide stock solution was prepared dissolving 0.62 mg lyso-Gb1-sulfatide (as delivered by Matreya) in 5 mL of 50% MeOH.

Subsequently the solution V1-A-626 was prepared as a mixture of 50 μL of lyso-Gb1-sulfatide stock solution and 10 mL 50% MeOH as displayed in the following:

| Label of resulting solution | exp. conc. [μg/mL] | Volume of solution [μL] | solution | volume of solvent [mL] | solvent |
|---|---|---|---|---|---|
| V1-A-626 | 0.60760 | 50 | lyso-Gb1-sulfatide-stock | 10 | 50% MeOH |

Subsequently the Calibration Standards were prepared by spiking solution V1-A-626 or higher concentrated Calibration Standards into blank human plasma from healthy people.

A detailed spiking scheme will be displayed in the following.

| Label of resulting solution | concentration [ng/mL] | Volume of solution [μL] | solution | volume of solvent [mL] | solvent | Volume [ml] |
|---|---|---|---|---|---|---|
| Std4B-626 | 5.0016 | 49.8 | V1-A-626 | 6 | human plasma | 6.0498 |
| Std3B-626 | 1.0003 | 1250 | Std4B-626 | 5 | human plasma | 6.25 |
| Std2B-626 | 0.19976 | 208 | Std4B-626 | 5 | human plasma | 5.208 |
| Std1B-626 | 0.050011 | 50.5 | Std4B-626 | 5 | human plasma | 5.0505 |

For calibration, calibration standards having four concentration levels between 0.05 and 5.00 ng/mL were used, namely Calibration Standards Std1B-626, Std2B-626, Std3B-626 and Std4B-626.

Preparation of Control Samples

Control samples were prepared by spiking solution V1-A-626 or a higher concentrated control sample into a blank human plasma.

A detailed spiking scheme will be displayed in the following.

| Label of resulting solution | concentration [ng/mL] | Volume of solution [μL] | solution | volume of blank matrix [mL] | Volume [ml] |
|---|---|---|---|---|---|
| QC-A2-626 | 0.30032 | 556 | QC-B7-626 | 5 | 5.556 |
| QC-B7-626 | 3.0010 | 27.3 | V1-A-626 | 5.5 | 5.5273 |

Blank Matrix

As a blank matrix, human plasma of a healthy subject was used containing no detectable levels of free lyso-Gb1-sulfatide. Before using such blank matrix for spiking lyso-Gb1-sulfatide should be determined in this matrix to assure the absence of it.

Study Samples
Preparation of Internal Standard

The Internal Standard (IS) stock solution was prepared dissolving 1.00 mg of lyso-Gb2 (as delivered by Matreya) in 2 mL of DMSO/MeOH (1/1; vol/vol).

Subsequently the Internal Standard Working Solution was prepared as a mixture of 82 μL of IS1 stock solution and 500 mL of ethanol. The ethanol may be purchased from any commercial source, wherein the ethanol is absolute ethanol having a grade suitable for the methods described herein. A person skilled in the art will recognize that proteins contained in 50 μl of a sample have to precipitate if 100 μL of said Internal Standard working solution are added to the sample.

Storing of Samples and Solutions

Control samples or study samples either were immediately stored below −20° C. at once or aliquots were transferred into new glass vials before storing under the same conditions.

Concentrated solutions (stock solutions, V1-A-534 etc.) as well as Internal Standard stock solutions were frozen below −20° C. pending next spiking.

Internal Standard working solution was stored below −20° C. until use.

The present inventors have found that free lyso-Gb1-sulfatide is stable in the above mentioned solutions. lyso-Gb1-Sulfatide is also stable at least for several weeks of storage in plasma/serum below −20° C. and over several freeze/thaw cycles in plasma/serum.

Sample Preparation for Analysis

All samples used in an analytical batch are prepared for analysis as follows:

Frozen samples were thawed at approximately 20 to 25° C. in a water bath taking from ambient conditions. After thawing the samples were mixed.

50 μL of the sample were transferred into a sample vial 100 μL of Internal Standard working solution (in EtOH) was added to the sample The thus obtained mixture was subsequently mixed using a DVX-2500 Multi-tube vortex device at 2500 rpm for about 30 seconds The thus obtained mixture was centrifuged for phase separation at 4000 rpm for 2 minutes.

Transfer of a volume of the supernatant adequate to injection purposes (approx. 100 µL) into appropriate (conical) auto-sampler vials Methods Chromatographic and Auto-Sampler Parameters The samples prepared for analysis as described above were subsequently subjected to the method described in the following:

| Parameter | Scheduled range/description | |
|---|---|---|
| Mobile phase solvent A | 50 mM FA in water | |
| Mobile phase solvent B | 50 mM FA in ACN/acetone (1:1; vol/vol) | |
| Chromatographic run | 0.0-0.5 min isocratic: | 10% B |
|  | 0.5-0.6 min step gradient: | 10% B → 33% B |
|  | 0.6-4.7 min linear gradient: | 33% B → 69% B |
|  | 4.7-5.4 min isocratic: | 100% B |
|  | 5.4-6.0 min isocratic: | 10% B |
| Flow | 1.1 mL/min | |
| Injection volume | 15 µL | |
| Injector flush | 0.1% TFA in 70% MeOH | |
| Column + Precolumn | YMC Pro C8, 100 × 3 mm ID, 3 µm | |
| Column temperature | 60° C. | |
| Retention time | approx. 4.3 to 4.9 min: | lyso-Gb1-sulfatide |
|  | approx. 2.6 to 3.3 min: | lyso-Gb 2 (IS) |

The YMC Pro C8 column (Nr. OS12S031003QT) used herein has been purchased from YMC, Germany.

It will be appreciated by a person skilled in the art that parameters where a "±" range is indicated represent parameters which may be adjusted between sequences. A sequence as used herein, preferably is a batch of defined numbers of samples, preferably 150 in maximum analyzed sequentially, wherein parameters comprising flow and temperature remain unchanged. Adjustments and calibrations performed between sequences are known to those skilled in the art and comprise exchange of the column.

These adjustments within the specified limits are minor changes and are recorded within the raw data of the study at the measuring station.

Detection

The thus prepared samples were subsequently subjected to the detection method the parameters of which are described in the following:

| MS Ionisation mode: | Electrospray Ionisation (ESI) |
|---|---|
| MS polarity: | positive |
| MS detection mode: | Multiple reaction monitoring (MRM) |
| Vaporizer temperature: | 550° C. ± 50° C. |
| Ionisation voltage: | 5.5 kV |
| Collisionally activated dissociation (CAD) gas: | Pressure = 5 psi |
| Gas 1: | Pressure = 57 psi |
| Gas 2: | Pressure = 67 psi |
| Curtain gas: | pressure = 39 psi |
| Lateral position: | 5 units |
| Vertical position: | 4 units |
| Quadrupole resolution | unit → unit |
| Transitions | 542.4 → 282.2 m/z lyso-Gb1-sulfatide (preferred quantifier) |
|  | 542.4 → 462.4 m/z lyso-Gb1-sulfatide (qualifier) |
|  | 624.5 → 282.2 m/z lyso-Gb2 (Internal Standard) |
| DP (declustering potential) | 50 V |

A person skilled in the art will acknowledge that methods for detecting free lyso-Gb1-sulfatide and/or determining the level of free lyso-Gb1-sulfatide in a sample from a subject using mass spectrometric analysis may also employ other transitions and fragments which allow for specific detection of and/or quantification of free lyso-Gb1-sulfatide in said sample from a subject.

Evaluation and Calculation of Results

To evaluate and to calculate results obtained with the above specified methods the following protocol were applied.

Rounding Procedure

Concentration data fed into and retrieved from the chromatographic data system (CDS) were rounded to five significant digits. Further calculations in the spreadsheet were performed to full computational accuracy and subsequently rounded to the significant digits/decimal places to be reported. Hence, deviations of intermediate results might occur caused by rounding. Accuracy and coefficients of variation (CV) will be reported with one and two decimal places, respectively.

Note Referring to the Rounding Procedure:

The last digit reported would be up-rounded if the subsequent digit was equal or greater than "5".

Regression and Statistics

Based on Calibration Standards the calibration curve fitting were established using the data processing software by means of peak area ratios (peak area of free lyso-substance contained in the sample from the subject/peak area of Internal Standard). Free lyso-substance concentrations were evaluated using an Internal Standard method A linear (y=ax+b) regression model using the weighting factor 1/conc. will be used to calculate the concentration of each analyte in every batch to be evaluated. The concentrations were calculated by means of the following formula:

$$\text{concentration} = \frac{\text{peak area ratio} - \text{intercept }(b)}{\text{slope }(a)}$$

Based thereon mean values, precision results (in terms of CVs) and accuracies (formula shown below) will be calculated using the program "Lotus 123".

$$\text{accuracy}(\%) = \frac{\text{calculated concentration}}{\text{expected concentration}} \cdot 100$$

Appropriate statistical models are described in e.g.

Green, J. R., Statistical Treatment of Experimental Data (Elsevier, New York, 1977), page 210 ff Lothar Sachs, Angewandte Statistik—Anwendung statistischer Methoden (Springer, Berlin, Heidelberg, New York, Tokyo 1984)

Software

Data acquisition, data processing, statistics and calculations were performed using Analyst® software 1.4.2 or higher (AB SCIEX, USA/Canada) as well as Lotus 1-2-3 97 or higher (Lotus Corp, USA).

Handbooks

Handbook   Arbeiten mit SmartSuite 97 (Lotus Development Corp., 1997)

-continued

| | |
|---|---|
| Documentation of software used | Documentation of Analyst ® Software (AB SCIEX, USA/Canada): Operator's Manual & Operator's Manual Addendum "New Functionality in Analyst 1.2" and Online Help System Analyst 1.4 (or higher) |

The protocols described 1 above were used to generate HPLC-mass spectrometric chromatograms of 150 plasma samples derived from the 150 subjects described in more details in Example 2. Exemplary HPLC-mass spectrometric chromatograms displaying peak intensity of free lyso-Gb1-sulfatide and IS of a healthy control person and of a patient diagnosed as MDL-positive are depicted in FIG. 1A and FIG. 1B.

More particularly, FIG. 1A shows HPLC-mass spectrometric chromatograms displaying peak intensity in cps of free lyso-Gb1-sulfatide (upper panel) and IS (lower panel) of a sample from a healthy subject as a function over the retention time in minutes. FIG. 1B shows HPLC-mass spectrometric chromatograms displaying peak intensity in cps of free lyso-Gb1-sulfatide (upper panel) and IS (lower panel) of a sample from an MLD patient as a function over the retention time in minutes.

The retention time of a substance as used herein, preferably is depicted on the x-axis and is the elapsed time between the time of injection of a solute, e.g. a biomarker according to the present invention and/or an internal standard, and the time of elution of the peak maximum of said solute. A person skilled in the art will acknowledge that the retention time of a substance according to the herein described methods is a unique characteristic of said solute and can be used for identification purposes. Internal Standard working solution comprising lyso-Gb2 as an internal standard was added to the sample as described above. It is important to understand that by said addition of IS to the sample, i.e. spiking of the sample, to be subjected to the method according to the present invention, the concentration of IS in the sample is known and by determining the area under the peak, i.e. the peak area, of the internal standard in said HPLC-mass spectrometric chromatogram the relation between a peak area and a concentration of a substance, e.g. of IS and/or a biomarker thus can be calculated. More precisely, a person skilled in the art will acknowledge that a peak area of a substance depicted in an HPLC-mass spectrometric chromatogram, such as the HPLC-mass spectrometric chromatogram depicted in FIG. 1A or FIG. 1B represents a measure for an amount of said substance subjected to an HPLC-mass spectrometric analysis. Moreover, a person skilled in the art will be able to calculate the amount of the substance in a sample from a subject subjected to an HPLC-mass spectrometric analysis, e.g. the amount of free lyso-Gb1-sulfatide in a sample subjected to the method of the present invention, using a ratio of the peak area of free lyso-Gb1-sulfatide, the amount of which is to be determined by said method and the peak area of IS, e.g. free lyso-Gb2; as well as calibration curves generated with said method and said free lyso-Gb1-sulfatide and/or IS. Accordingly, this allows subsequently for determining a level of free lyso-Gb1-sulfatide.

With regard to free lyso-Gb1-sulfatide<LLOQ (limit of determination) has been replaced by 0.025, which refers to half of the limit of detection.

Example 2: Genetic Testing and Classification of Study Participants

After consenting of patients to participation in the study, patients were subjected to a genetic testing for mutations of the gene coding for ARSA. Accordingly, 5 to 10 ml of EDTA blood were sequenced according to Seeman et al. (Seeman et al., 1995; Seeman, N. C. (1995) J. Am. Chem. Soc. 117, 1194-1200; N. C. Seeman, Biochemistry 34, 673-682 (1995); N. C. Seeman, Structural Domains of DNA Mesojunctions, Biochemistry 34, 920-929 (1995); N. C. Seeman, The Chemical Intelligencer 1(3), 38-47 (1995); N. C. Seeman, Journal of the Chemical Society, Chemical Communications, 2249-2250 (1995)). Were appropriate other genes beside the gene coding for ARSA were sequenced in addition, particularly in controls. Said genetic testing was controlled using test samples of age and sex matched control patients.

Plasma samples from a first cohort of 93 subjects were analyzed.

The level of free lyso-Gb1-sulfatide in samples of said 93 subjects was determined according to the method described in Example 1. Table 1 shows the median and minimum and maximum levels of free lyso-Gb1-sulfatide in said samples of said 93 subjects. As is evident from said Table 1, MLD patients could be clearly distinguished from subjects suffering from other LSDs. Such other LSDs included Fabry disease, Gaucher's disease and Nieman-Pick disease type C.

TABLE 1

| | MLD | other LSD's | p |
|---|---|---|---|
| n | 25 | 68 | |
| median (IQR) | 0.35 (0.19-0.62) | 0.05 (0.05-0.05) | <0.001 |
| min-max | 0.05-1.49 | 0.05-0.05 | |

Plasma samples from a second cohort of 150 subjects were analyzed, whereby such second cohort comprised the first cohort.

The level of free lyso-Gb1-sulfatide in samples of said 150 subjects was determined according to the method described in Example 1. In connection with said second cohort of 150 patients 183 samples have been analysed. That total group comprises 25 MLD patients, 3 carriers, 6 healthy controls and 116 patients with other lysosomal storage disorders: 5 Gaucher patients (27 samples), 20 Fabry unclear patients (20 samples), 11 male Fabry patients (15 samples), 9 Female Fabry patients (11 samples), 7 NPC1 patients (9 samples), 6 NPC1 carriers (9 samples), 5 NPA/B patients (5 samples), 6 Krabbe disease patients (6 samples), 8 male Hunter disease patients (8 samples), 2 female Hunter disease patients (2 samples), 3 GM1 gangliosidosis patients (3 samples), 3 San Filippo B patients (MPS3b) (3 samples), 9 MPS6 patients (9 samples), 1 MPS6 carrier (1 sample), 1 Tay-Sachs disease patient (1 sample), 4 MPS1 (4 samples), 3 San Filippo A patients (MPS3a) (3 samples), 12 MPS3a patients (Morquio) (12 samples) and 1 MPS3a carrier (Morquio) (1 sample). Upon stratifying these patients into healthy controls ("healthy controls"), patients suffering from MLD ("MLD"), patients being MLD carrier ("MLD carrier"), patients suffering from other lysosomal storage diseases ("other LSD") results in a cohort composition summarized in Table 2.

TABLE 2

| | frequency | percentage |
|---|---|---|
| Healthy controls | 6 | 4.0 |
| MLD | 25 | 16.7 |
| MLD carrier | 3 | 2.0 |
| Other LSD | 116 | 77.3 |
| Total | 150 | 100.0 |

Figure 2:
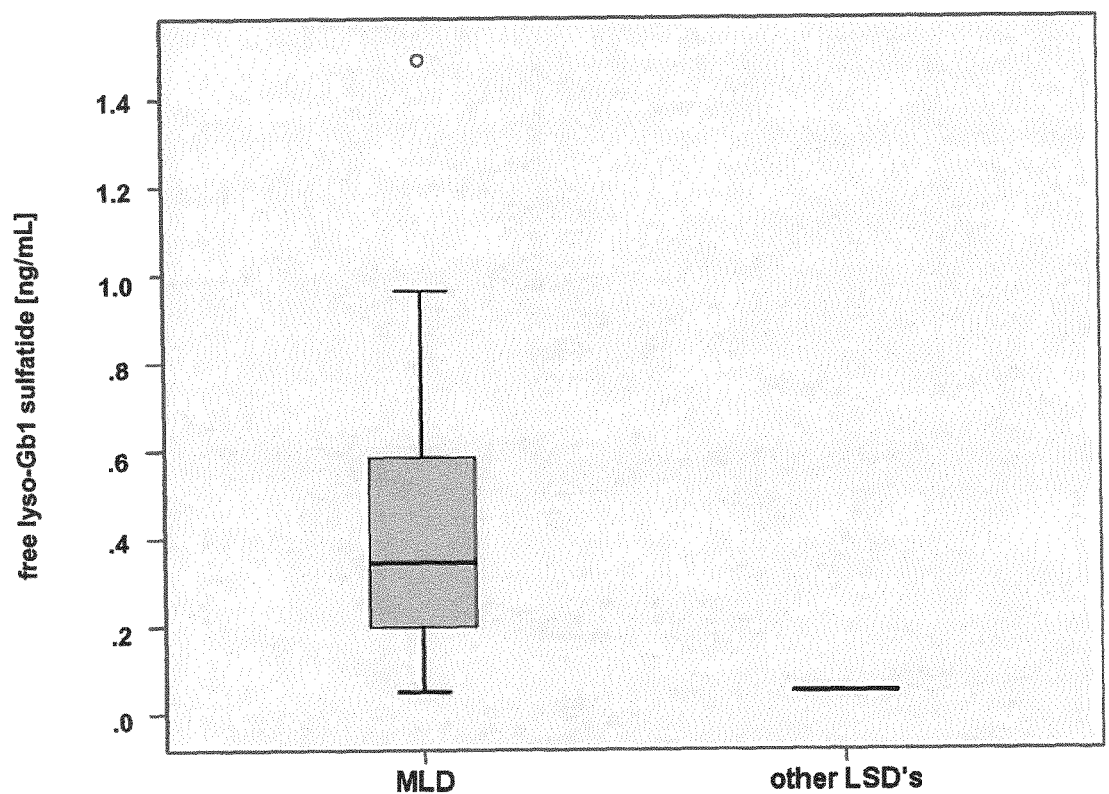
FIG. 2 is a boxplot indicating levels in a first cohort of MLD diagnosed subjects of free lyso Gb1-sulfatide in ng/ml plasma compared to the levels in subjects positively diagnosed as suffering from other LSDs of free lyso Gb1-sulfatide in ng/ml plasma.

The results from the analysis of the second cohort are depicted in FIG. 2.

FIG. 2 is a boxplot indicating levels of free lyso-Gb1 sulfatide; the y-axis indicates the absolute levels of free lyso-Gb1-sulfatide in ng/ml determined in plasma of patients by the method according to the present invention, wherein the x-axis depicts groups of patients, which have been grouped as described. The boxplot represents the 25th and 75th percentile of each group of patients by the bottom and top of the box, respectively; the band near the middle of the box represents the 50th percentile (i.e. the median) of each group; The whiskers represent one standard deviation above and below the mean of the data; Any data not included between the whiskers is shown as an outlier with a small circle.

Example 3: Diagnosis of MLD Using Free Lyso-Gb1-Sulfatide as a Biomarker

Plasma samples from the first cohort of patients defined in Example 1 were subject to the methods and analysis described in Example 1. The results from said analysis are depicted in FIG. 2

FIG. 2 is a boxplot indicating levels of free lyso-Gb1-sulfatide in patients diagnosed either as MLD positive or as suffering from other LSDs. The y-axis demonstrates the levels of free lyso-Gb1-sulfatide in ng/ml determined in plasma of patients by the method of Example 1, wherein the x-axis depicts groups of patients, which have been grouped as described in Example 2. The boxplot represents the $25^{th}$ and $75^{th}$ percentile of each group of patients by the bottom and top of the box, respectively; the band near the middle of the box represents the $50^{th}$ percentile (i.e. the median) of each group; the whiskers represent one standard deviation above and below the mean of the data. Any data not included between the whiskers is shown as an outlier with a small circle or star.

Plasma samples from the second cohort of patients defined in Example 1 were subject to the methods and analysis described in Example 1. The results from said analysis are depicted in FIG. 3.

Figure 3:
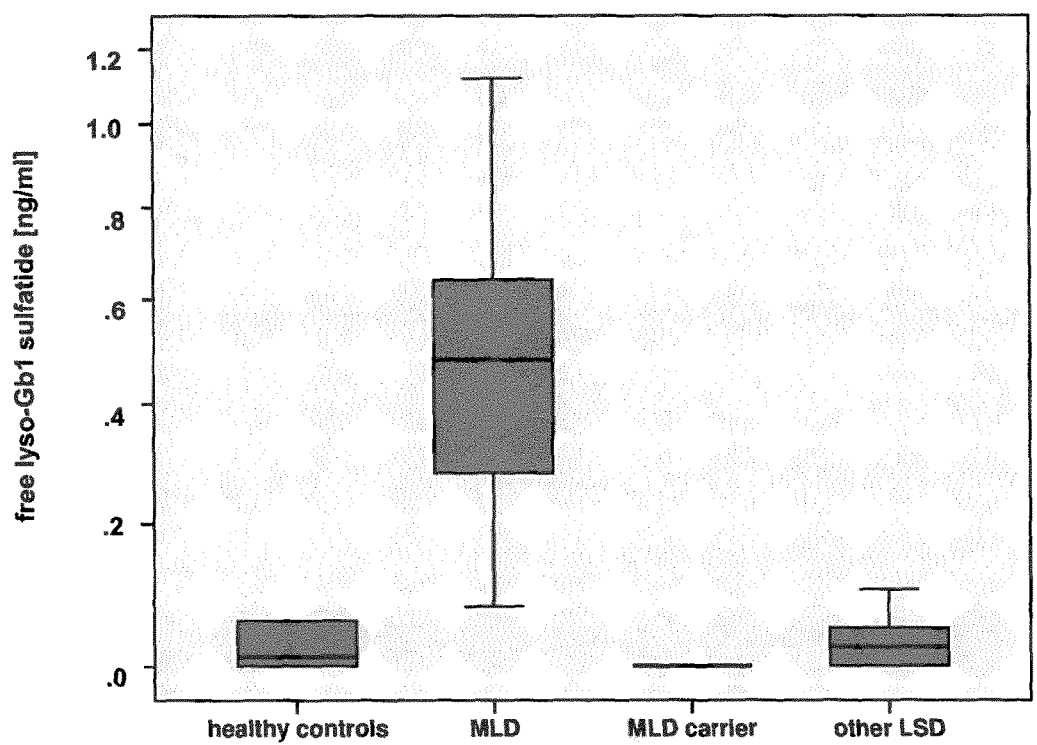
FIG. 3 is a boxplot indicating levels in a second cohort of MLD diagnosed subjects of free lyso Gb1-sulfatide in ng/ml plasma compared to the levels in subjects positively diagnosed as suffering from other LSDs of free lyso Gb1-sulfatide in ng/ml plasma, in subjects positively diagnosed as being MLD carrier of free lyso Gb1-sulfatide in ng/ml plasma, and in subjects being healthy controls.

FIG. 3 is a boxplot indicating levels of free lyso-Gb1 sulfatide; The y-axis indicates the absolute levels of free lyso-Gb1-sulfatide in ng/ml determined in plasma of patients by the method of Example 1, wherein the x-axis depicts groups of patients, which have been grouped as described (healthy controls, patients suffering from MLD, patients being MLD carrier and patients suffering from LSD different from MLD). The boxplot represents the 25th and 75th percentile of each group of patients by the bottom and top of the box, respectively; the band near the middle of the box represents the 50th percentile (i.e. the median) of each group. The whiskers represent one standard deviation above and below the mean of the data. Any data not included between the whiskers is shown as an outlier with a small circle.

For the second cohort of patients the activity of arylsulfatase A was determined in plasma using standard fluorometric procedures. The results from said analysis are depicted in FIG. 4.

FIG. 4 is a boxplot indicating the arylsulfatase enzyme activity in the groups defined above. The y-axis demonstrates the arylsulfatase enzyme given as U/mg protein, wherein the x-axis depicts groups of patients, which have been grouped as described above. The boxplot represents the 25th and 75th percentile of each group of patients by the bottom and top of the box, respectively; the band near the middle of the box represents the 50th percentile (i.e. the median) of each group; the whiskers represent one standard deviation above and below the mean of the data; any data not included between the whiskers is shown as an outlier with a small circle or star.

For comparing the diagnostic value of the different biomarkers, namely free lyso-Gb1-sulfatide and enzymatic activity of arylsulfatase A, and for the calculation of correlations between the two biomarkers the data obtained by the method described above was first aggregated by using the first measured value of every marker for MLD patient.

Paired sample statistical techniques were used for the comparison of two biomarkers. The method exploits the mathematical equivalence of the AUC to the Mann-Whitney U-statistic (Delong E. R., Delong D. M., Clarke-Pearson D. L., 1988, Biometrics, 44, 837-45.).

The accuracy of levels of the different biomarkers (free lyso-Gb1-sulfatide) obtained by the method described in Example 1 above was evaluated to discriminate patients with MLD from patients without having MLD using Receiver Operating Characteristic (ROC) curve analysis (Metz C. E., 1978, *Semin Nucl Med*, 8, 283-98; Zweig M. H., Campbell G., 1993, *Clin Chem*, 39, 561-77).

The ROC curves were calculated using PASW Statistics 18, Release Version 18.0.2 (© SPSS, Inc., 2009, Chicago, Ill., www.spss.com). The comparisons of ROC curves and the linear mixed models were done using SAS software, Version 9.2 of the SAS System for Windows. (© 2008 SAS Institute Inc., Cary, N.C., USA).

The respective ROC curve is shown in FIG. 5.

FIG. 5 is a graph showing receiver operating characteristics (ROC) curves of free lyso-Gb1-sulfatide and arylsulfatase A. The x-axis represents "1-specificity" and the y-axis represents the sensitivity. Free lyso-Gb1-sulfatide demonstrates a 98% sensitivity and 99.1% specificity, wherein arylsulfatase A has at best a sensitivity of 92.1% and 94% specificity, respectively.

The results are also summarized in Table 3.

TABLE 3

|  | Enzymatic activity of ARSA [U/mg protein] (n = 150/incl. 25 mld) | Free lyso-Gb1 sulfatide [ng/ml] (n = 150/incl. 25 mld) |
| --- | --- | --- |
| Cut point | <56 | >0.011 |
| Sensitivity | 92.1% | 98.0% |
| Specificity | 94.0% | 99.1% |
| AUC and 95%CI in ROC Analysis | 0.992 (0.957-1.000) | 0.997 (0.992-1.000) |

Example 4: Incorrect Diagnosis of a Patient as MLD Positive Based on Enzymatic Activity of Arylsulfatase A Two patients demonstrated a pathological reduced enzyme activity for aylsulfatse; however the lyso-Gb1-sulfatide was normal; one patient was homozygous for the mutation p.N352S, the second one was compound heterozygous.

In HGMD database (Human Gene Mutation Database at the Institute of Medical Genetics in Cardiff) this mutation p.N352S is published in 3 articles (Gieselmann 1989, Proc. Natal. Acad. Sci USA; 86(23): 9436-40; Baronica 2011, Coll Antropol. 2011 January; 35 Suppl 1:11-6; and Rickettes 1996, Am J Med Genet. 67(4): 387-92). They associate p.N352S with ASA pseudodeficiency (in vitro and in vivo studies show that this allele has a normal stability and activity, but predicted to be less stable and less active). Gieselmann 1989 shows as well that ARSA activity in tissues from compound heterozygous individuals is lower than homozygous p.N352S individuals. This is a disease-associated polymorphism in HGMD and, most importantly, in dbSNP (rs2071421) the minor allele frequency for this SNP is 20% in the general population and varies between 13-39% in the several hapmap populations. Finally, Poly-Phen prediction is "benign" (probability of being a mutation is 1.2%).

The features of the present invention disclosed in the specification, the claims, the sequence listing and/or the drawings may both separately and in any combination thereof be material for realizing the invention in various forms thereof.

The invention claimed is:

1. A method for generating quantitative data for a subject comprising: determining by means of mass spectrometric analysis a level of a free lyso-Gb1-sulfatide present in a sample from the subject, wherein the sample is a whole blood sample collected from the subject on a dry blood filter card, wherein the mass spectrometric analysis is carried out from the collected whole blood on the dry blood filter card and wherein lyso-Gb1-sulfatide is of formula (I)

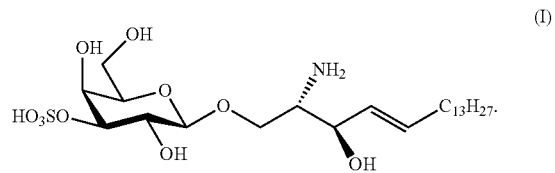

wherein the subject is suffering from metachromatic leukodystrophy, or is suspected of suffering from metachromatic leukodystrophy.

2. The method of claim 1, wherein the mass spectrometric analysis is selected from the group comprising SELDI, MALDI, MALDI-Q TOF, MS/MS, TOF-TOF and ESI-O-TOF.

3. The method of claim 1, wherein the mass spectrometric analysis is combined with high performance liquid chromatography (HPLC).

* * * * *